(12) United States Patent
Abe et al.

(10) Patent No.: US 9,116,093 B2
(45) Date of Patent: Aug. 25, 2015

(54) BLOOD ANALYZER, BLOOD ANALYSIS METHOD, AND COMPUTER PROGRAM PRODUCT

(75) Inventors: Masaki Abe, Hamburg (DE); Ayumu Yoshida, Kobe (JP); Jo Linssen, Kerkrade (NL)

(73) Assignee: SYSMEX CORPORATION, Kobe, Hyogo (JP)

( * ) Notice: Subject to any disclaimer, the term of this patent is extended or adjusted under 35 U.S.C. 154(b) by 0 days.

(21) Appl. No.: 13/462,236

(22) Filed: May 2, 2012

(65) Prior Publication Data
US 2012/0282601 A1 Nov. 8, 2012

(30) Foreign Application Priority Data
May 5, 2011 (EP) .................................... 11164911

(51) Int. Cl.
| | | |
|---|---|---|
| *G01N 15/14* | (2006.01) | |
| *G01N 35/02* | (2006.01) | |
| G01N 21/51 | (2006.01) | |
| G01N 21/47 | (2006.01) | |
| G01N 21/64 | (2006.01) | |
| G01N 15/10 | (2006.01) | |
| G01N 35/04 | (2006.01) | |

(52) U.S. Cl.
CPC .......... *G01N 15/1459* (2013.01); *G01N 35/026* (2013.01); *G01N 21/51* (2013.01); *G01N 2015/1006* (2013.01); *G01N 2021/4707* (2013.01); *G01N 2021/4726* (2013.01); *G01N 2021/6441* (2013.01); *G01N 2035/0415* (2013.01)

(58) Field of Classification Search
None
See application file for complete search history.

(56) References Cited

U.S. PATENT DOCUMENTS

| | | | |
|---|---|---|---|
| 5,677,183 A * | 10/1997 | Takarada et al. | 436/10 |
| 6,004,816 A * | 12/1999 | Mizukami et al. | 436/10 |
| 6,228,652 B1 * | 5/2001 | Rodriguez et al. | 436/63 |
| 7,916,280 B2 * | 3/2011 | Ueno et al. | 356/39 |
| 7,960,099 B2 * | 6/2011 | Xu et al. | 435/2 |
| 2007/0020721 A1 * | 1/2007 | Yoshida et al. | 435/34 |
| 2007/0231913 A1 | 10/2007 | Tsuji et al. | |
| 2009/0023129 A1 | 1/2009 | Xu et al. | |

(Continued)

FOREIGN PATENT DOCUMENTS

JP   2006-091024 A   4/2006

OTHER PUBLICATIONS

Herklotz et al., Precision and Accuracy of the Leukocyte Differential on the Sysmex XE-2100, Sysmex Journal International, vol. 11, No. 1, pp. 8-21, 2001.*

Inoue, Hiroyuki, "Overview of Automated Hematology Analyzer XE-2100™," Sysmex Journal International, vol. 9, No. 1, 1999, pp. 58-64.

(Continued)

*Primary Examiner* — Thuy Nguyen
*Assistant Examiner* — Rebecca Martinez
(74) *Attorney, Agent, or Firm* — Brinks Gilson & Lione

(57) ABSTRACT

A blood analyzer, a blood analysis method, and a computer program product that can distinguishably detect abnormal lymphocytes, blasts, and atypical lymphocytes are provided. A blood analyzer prepares a first measurement sample from a first reagent containing a hemolyzing agent, a second reagent containing a fluorescence staining dye, and the blood specimen, and prepares a second measurement sample from a third reagent containing a hemolyzing agent, a fourth reagent containing a fluorescence staining dye, and the blood specimen. The blood analyzer measures each of the measurement samples, and distinguishably detects abnormal lymphocytes, blasts, and atypical lymphocytes in a blood specimen based on the measurement data.

20 Claims, 18 Drawing Sheets

(56) References Cited

U.S. PATENT DOCUMENTS

2010/0151509 A1   6/2010   Ting et al.
2010/0248247 A1   9/2010   Kataoka et al.
2011/0059861 A1 *   3/2011   Nolan et al. .................... 506/10

OTHER PUBLICATIONS

Office Action from counterpart Chinese Application No. 201210138044.1, dated Dec. 30, 2013, 47 pages (with translation).

* cited by examiner

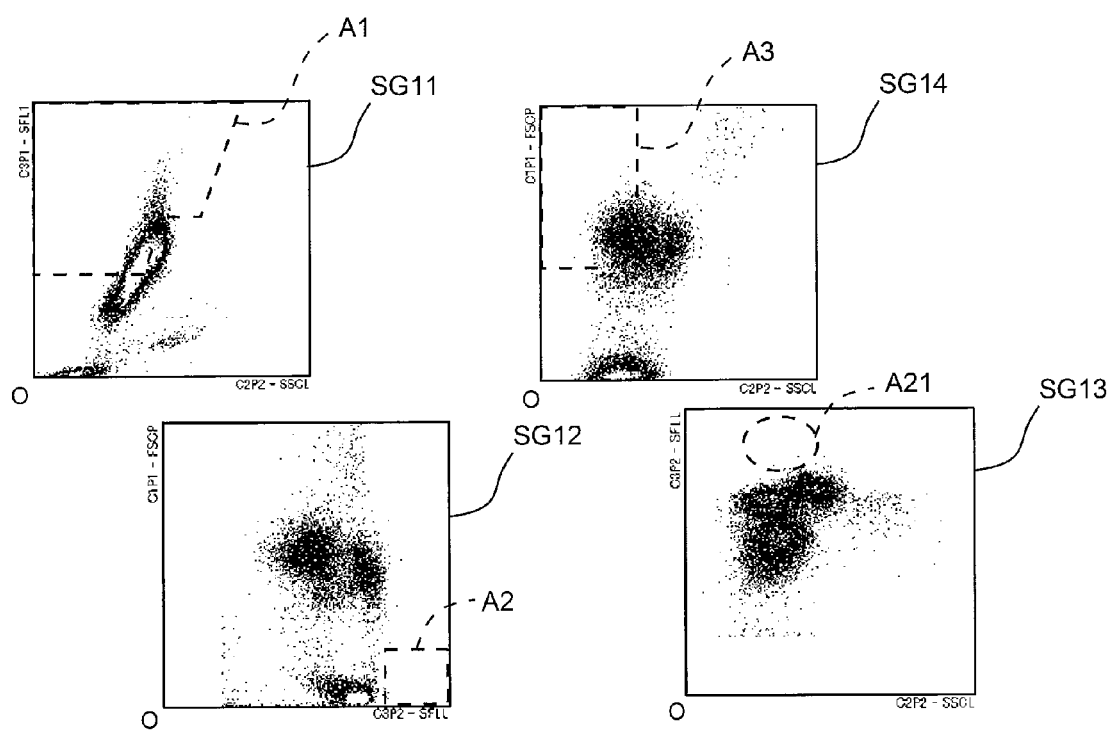

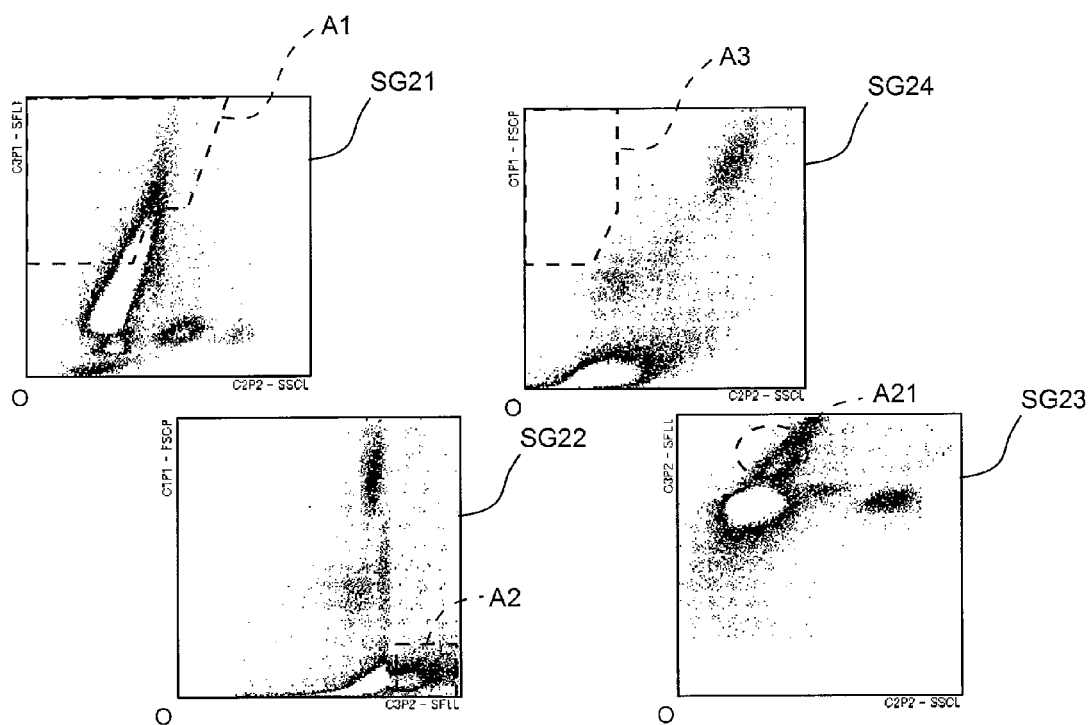

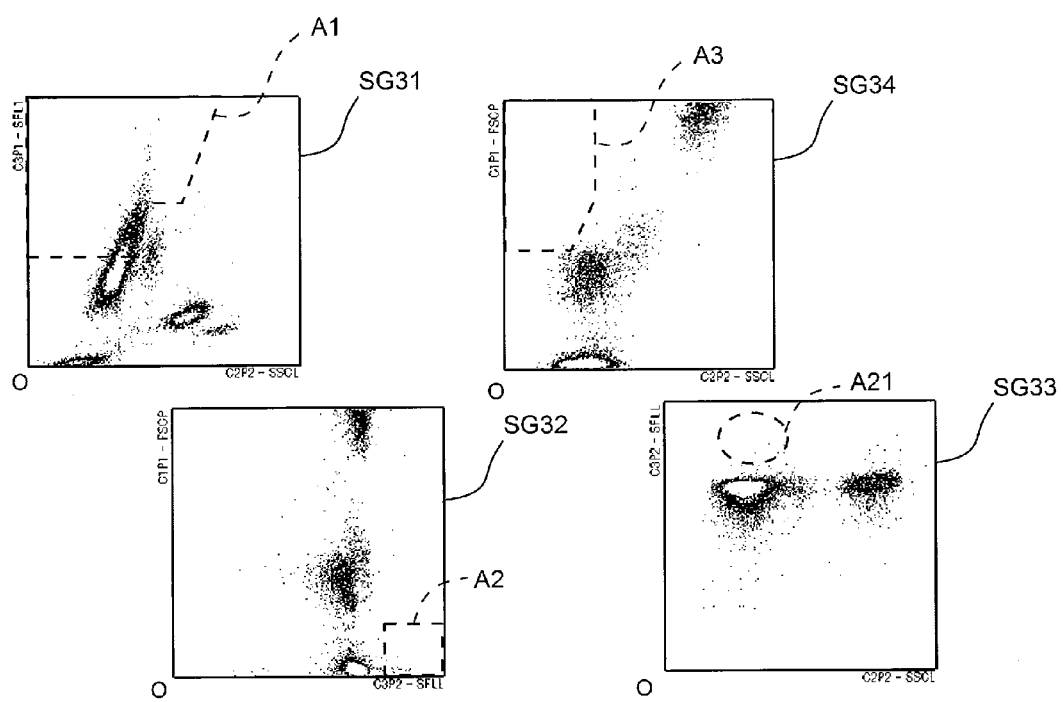

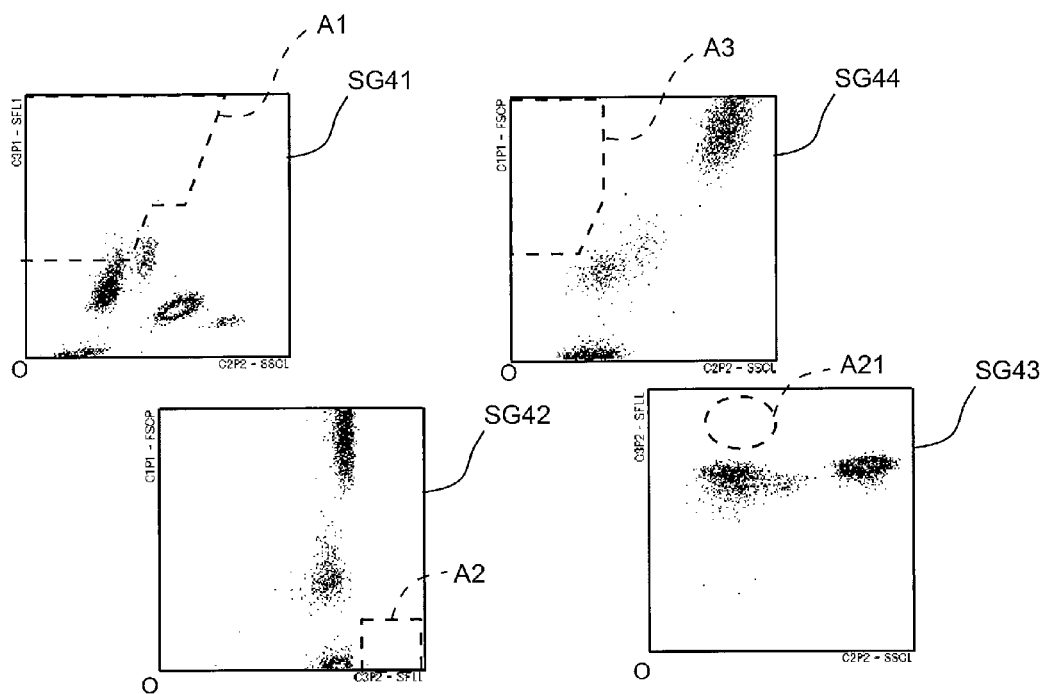

BLOOD ANALYZER, BLOOD ANALYSIS METHOD, AND COMPUTER PROGRAM PRODUCT

RELATED APPLICATIONS

This application claims priority under 35 U.S.C. §119 to European Patent Application No. 11164911.7 filed on May 5, 2011, the entire content of which is hereby incorporated by reference.

BACKGROUND OF THE INVENTION

1. Field of the Invention

The present invention relates to a blood analyzer and a blood analysis method for optically measuring a blood specimen and classifying hemocytes contained in the blood specimen, and a computer program product for enabling a computer to analyze blood.

2. Description of the Related Art

Five types of leukocyte consisting of lymphocytes, monocytes, basophils, eosinophils, and neutrophils are present in normal peripheral blood, and many blood cell counting apparatuses have the function of classifying leukocytes contained in a blood specimen into the five types. On the other hand, cells that are not present in normal peripheral blood appear in peripheral blood affected with diseases such as viral infectious diseases and hematopoietic system diseases. Abnormal leukocytes that appear in peripheral blood include abnormal mononuclear leukocytes, which can be largely categorized into reactive abnormal mononuclear leukocytes and neoplastic abnormal mononuclear leukocytes. Reactive abnormal mononuclear leukocytes include "atypical lymphocytes", which can be observed for viral infection, drug allergy, and the like. Neoplastic abnormal mononuclear leukocytes can be further categorized into neoplastic mature abnormal mononuclear leukocytes and neoplastic immature abnormal mononuclear leukocytes. Neoplastic mature mononuclear leukocytes include "abnormal lymphocytes", which can be observed for e.g. chronic lymphocytic leukemia (CLL). Neoplastic immature mononuclear leukocytes include "blasts", which can be observed for e.g. acute leukemia. Distinguishably detecting atypical lymphocytes, abnormal lymphocytes, and blasts in peripheral blood is very useful in screening or diagnosis of diseases as described above.

Japanese Laid-Open Patent Publication No. 2006-91024 discloses detecting atypical lymphocytes and myeloblasts distinguishably from normal leukocytes using reagents for classifying leukocytes into four or five categories (see FIGS. 12 and 14). U.S. Patent Publication No. 2009/0023129 discloses detecting a cell group consisting of abnormal lymphocytes and blasts distinguishably from normal leukocytes using reagents for classifying leukocytes into five categories (see FIG. 2). The techniques disclosed in these documents are similar in that they use a hemolyzing agent containing a cationic surfactant and a nonionic surfactant, and a stain solution containing a fluorescent dye for staining nucleic acid as the reagents for classifying leukocytes. However, atypical lymphocytes, abnormal lymphocytes, and blasts appear in substantially the same area for fluorescence intensity and scattered light intensity in Japanese Laid-Open Patent Publication No. 2006-91024 and U.S. Patent Publication No. 2009/0023129, and therefore cannot be distinguished from one another.

U.S. Patent Publication No. 2007/231913 discloses detecting myeloblasts distinguishably from mature leukocytes and immature granulocytes using predetermined reagents (see FIGS. 1, 2, and 5). This document discloses, as the above-described reagents, a hemolyzing agent containing a nonionic surfactant and a solubilizing agent, and a fluorescent dye for staining nucleic acid. U.S. Patent Publication No. 2010/248247 discloses distinguishably detecting lymphoblasts, myeloblasts, mature leukocytes, and immature granulocytes using predetermined reagents (see FIGS. 13A and 13B). This document discloses, as the above-described reagents, a hemolyzing agent containing a nonionic surfactant and a solubilizing agent, and a fluorescent dye for staining nucleic acid. However, neither U.S. Patent Publication No. 2007/231913 nor U.S. Patent Publication No. 2010/248247 discloses detecting atypical lymphocytes distinguishably from abnormal lymphocytes.

SUMMARY OF THE INVENTION

The scope of the present invention is defined solely by the appended claims, and is not affected to any degree by the statements within this summary.

A first aspect of the present invention is a blood analyzer comprising: a dispensing portion configured to dispense a first blood specimen and a second blood specimen from a blood specimen; a sample preparation portion configured to prepare a first measurement sample from the first blood specimen dispensed by the dispensing portion, a first fluorescent dye for staining nucleic acid, and a first hemolyzing agent containing a cationic surfactant, and configured to prepare a second measurement sample from the second blood specimen dispensed by the dispensing portion, a second fluorescent dye for staining nucleic acid, and a second hemolyzing agent not containing a cationic surfactant but containing another surfactant; a light source configured to irradiate light onto each of the first measurement sample and the second measurement sample prepared by the sample preparation portion; a light-receiving portion configured to receive a fluorescence and a scattered light from the first measurement sample irradiated with light by the light source and output a first fluorescence signal relating to the received fluorescence and a first scattered light signal relating to the received scattered light, and configured to receive a fluorescence and a scattered light from the second measurement sample irradiated with light by the light source and output a second fluorescence signal relating to the received fluorescence and a second scattered light signal relating to the received scattered light; an information processing portion configured to distinguishably detect an atypical lymphocyte, an abnormal lymphocyte and a blast from the blood specimen based on the first fluorescence signal, the first scattered light signal, the second fluorescence signal and the second scattered light signal; and an output portion configured to output a result of the detection made by the information processing portion.

A second aspect of the present invention is a blood analyzer comprising: a dispensing portion configured to dispense a first blood specimen and a second blood specimen from a blood specimen; a sample preparation portion configured to prepare a first measurement sample from the first blood specimen dispensed by the dispensing portion, a first fluorescent dye for staining nucleic acid, and a first hemolyzing agent containing a cationic surfactant, and configured to prepare a second measurement sample from the second blood specimen dispensed by the dispensing portion, a second fluorescent dye for staining nucleic acid, and a second hemolyzing agent not containing a cationic surfactant but containing another surfactant; a light source configured to irradiate light onto each of the first measurement sample and the second measurement sample prepared by the sample preparation portion; a light-receiving portion configured to receive a fluorescence and a scattered light from the first measurement sample irradiated with light by the light source and output a first fluorescence signal relating to the received fluorescence and a first scattered light signal relating to the received scattered light, and configured to receive a fluorescence and a scattered light from the second measurement sample irradiated with light by the light source and output a second fluorescence signal relating to the received fluorescence and a second scattered light signal relating to the received scattered light; an information processing portion configured to distinguishably detect a reactive abnormal mononuclear leukocyte and a neoplastic abnormal mononuclear leukocyte, based on the first fluorescence signal, the first scattered light signal, the second fluorescence signal and the second scattered light signal; and an output portion configured to output a result of the detection made by the information processing portion.

A third aspect of the present invention is a blood analysis method comprising: dispensing a first blood specimen from a blood specimen; preparing a first measurement sample from the dispensed first blood specimen, a first fluorescent dye for staining nucleic acid, and a first hemolyzing agent containing a cationic surfactant; irradiating light onto the prepared first measurement sample; receiving a fluorescence and a scattered light from the first measurement sample irradiated with light, and obtaining a first fluorescence signal relating to the received fluorescence and a first scattered light signal relating to the received scattered light; dispensing a second blood specimen from the blood specimen; preparing a second measurement sample from the dispensed second blood specimen, a second fluorescent dye for staining nucleic acid, and a second hemolyzing agent not containing a cationic surfactant but containing another surfactant; irradiating light onto the prepared second measurement sample; receiving a fluorescence and a scattered light from the second measurement sample irradiated with light, and obtaining a second fluorescence signal relating to the received fluorescence and a second scattered light signal relating to the received scattered light; distinguishably detecting an atypical lymphocyte, an abnormal lymphocyte and a blast from the blood specimen, based on the first fluorescence signal and the first scattered light signal, the second fluorescence signal and the second scattered light signal; and outputting a result of the detection.

A fourth aspect of the present invention is a computer program product comprising: a computer readable medium, and software instructions, on the computer readable medium, for enabling a computer to perform operations comprising: receiving a first fluorescence signal and a first scattered light signal relating to a fluorescence and a scattered light that are generated when light is irradiated onto a first measurement sample prepared from a first blood specimen dispensed from a blood specimen, a first fluorescent dye for staining nucleic acid, and a first hemolyzing agent containing a cationic surfactant; receiving a second fluorescence signal and a second scattered light signal relating to a fluorescence and a scattered light that are generated when light is irradiated onto a second measurement sample prepared from a second blood specimen dispensed from the blood specimen, a second fluorescent dye for staining nucleic acid, and a second hemolyzing agent not containing a cationic surfactant but containing another surfactant; distinguishably detecting an atypical lymphocyte, an abnormal lymphocyte and a blast from the blood specimen, based on the first fluorescence signal, the first scattered light signal, the second fluorescence signal and the second scattered light signal; and outputting a result of the detection.

BRIEF DESCRIPTION OF THE DRAWINGS

The invention, together with objects and advantages thereof, may best be understood by reference to the following description of the presently preferred embodiments together with the accompanying drawings in which:

FIG. 14A shows examples of scattergrams obtained when measuring a blood specimen collected from a patient with acute myelocytic leukemia;

FIG. 14B shows examples of scattergrams obtained when measuring a blood specimen collected from a patient with chronic lymphocytic leukemia;

FIG. 14C shows examples of scattergrams obtained when measuring a blood specimen containing atypical lymphocytes;

FIG. 14D shows examples of scattergrams obtained when measuring a normal blood specimen.

DETAILED DESCRIPTION OF THE PREFERRED EMBODIMENTS

Preferred embodiments of the present invention will now be described below with reference to the accompanying drawings.

Configuration of Blood Analyzer

Figure 1:
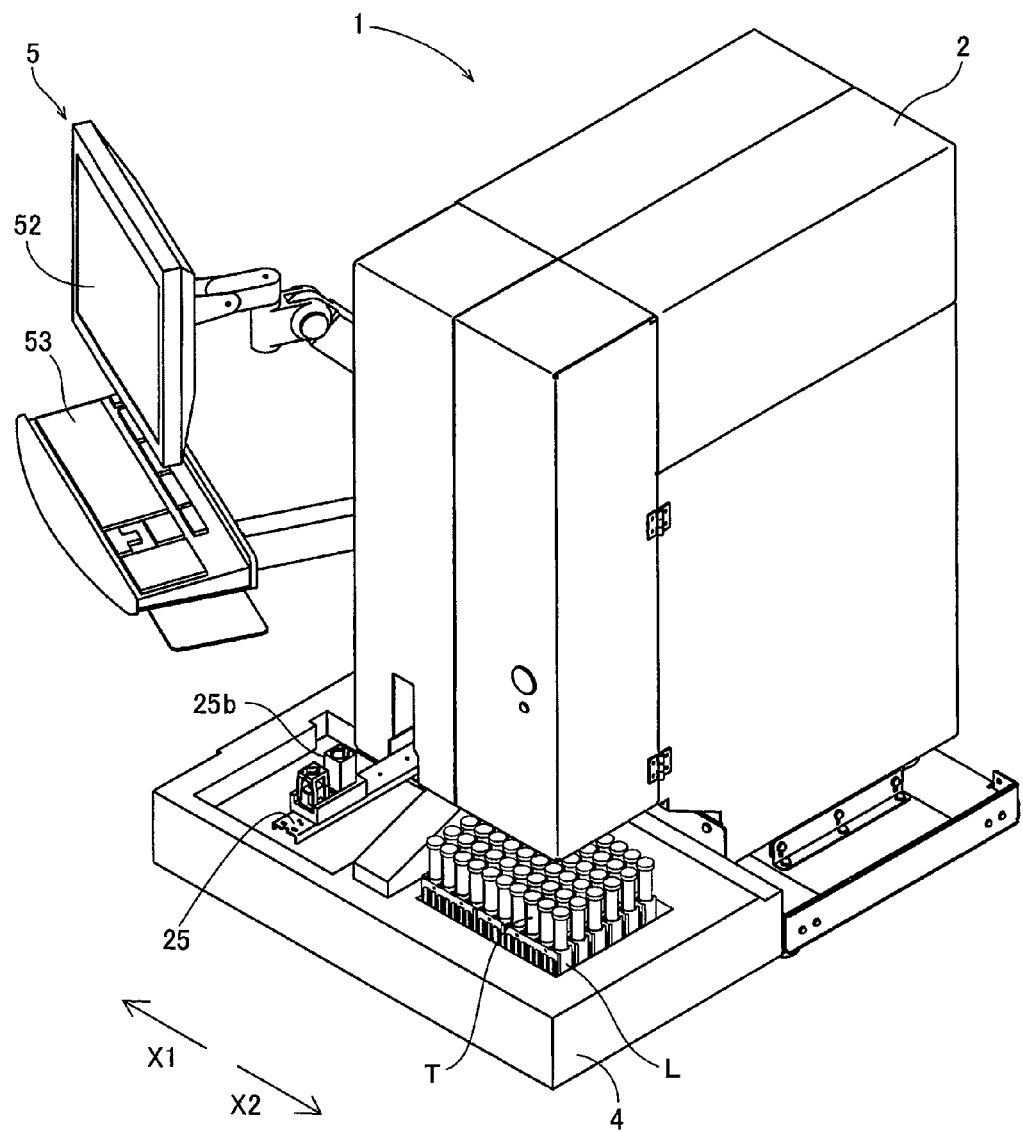
FIG. 1 is a perspective view showing an external appearance of a blood analyzer according to an embodiment.

FIG. 1 is a perspective view showing an external appearance of a blood analyzer according to this embodiment. A blood analyzer 1 according to this embodiment is a multiple-item hemocyte analyzer for detecting hemocytes contained in a blood specimen, such as leukocytes, erythrocytes, and platelets, and counting each type of the hemocyte. As shown in FIG. 1, the blood analyzer 1 includes a measurement unit 2, a specimen carrying unit 4 disposed on the front side of the measurement unit 2, and an information processing unit 5 that can control the measurement unit 2 and the specimen carrying unit 4.

A blood specimen that is peripheral blood collected from a patient is housed in a specimen container (blood collecting tube). A plurality of specimen containers are held in a sample rack, and the sample rack is carried by the specimen carrying unit 4, and thereby the blood specimen is supplied to the measurement unit 2.

Configuration of Measurement Unit

Figure 2:
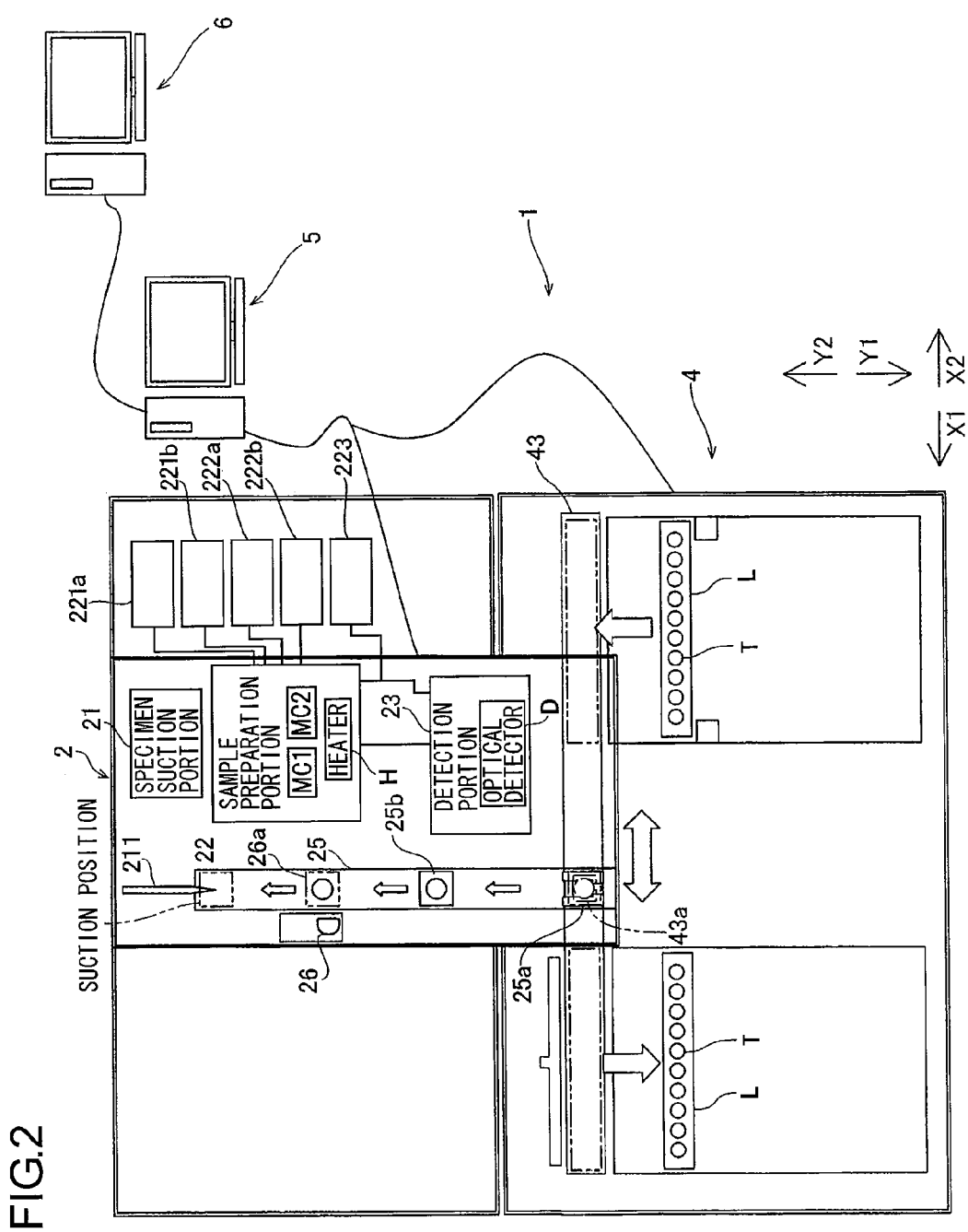
FIG. 2 is a block diagram showing the configuration of a measurement unit according to the embodiment.

The configuration of the measurement unit will now be described. FIG. 2 is a block diagram showing the configuration of the measurement unit. As shown in FIG. 2, the measurement unit 2 includes a specimen suction portion 21 that sucks blood as a specimen from the specimen container (blood collecting tube) T, a sample preparation portion 22 that prepares a measurement sample used for measurement from the blood sucked by the specimen suction portion 21, and a detection portion 23 that detects hemocytes in the measurement sample prepared by the sample preparation portion 22. The measurement unit 2 further includes an inlet (see FIG. 1) for taking, into the measurement unit 2, the specimen container T housed in the sample rack L carried by a rack carrying portion 43 of the specimen carrying unit 4, and a specimen container carrying portion 25 that takes the specimen container T from the sample rack L into the measurement unit 2 and carries the specimen container T to a suction position where blood is sucked by the specimen suction portion 21.

As shown in FIG. 2, the specimen suction portion 21 includes a suction tube 211. The specimen suction portion 21 also includes a syringe pump. Furthermore, the suction tube 211 is vertically movable, and is configured to suck the blood contained in the specimen container T that has been carried to the suction position when moved downward.

The sample preparation portion 22 includes a first mixing chamber MC1 and a second mixing chamber MC2. The suction tube 211 sucks a predetermined amount of a whole blood specimen from the specimen container T using the syringe pump. The specimen thus sucked is transferred to the position of the first mixing chamber MC1 and the second mixing chamber MC2, and a predetermined amount of the whole blood specimen is dispensed to each of the chambers MC1 and MC2 using the syringe pump. The sample preparation portion 22 also includes a heater H for heating the first mixing chamber MC1 and the second mixing chamber MC2.

The sample preparation portion 22 is connected via a tube with a reagent container 221a for housing a first reagent, a reagent container 221b for housing a second reagent, a reagent container 222a for housing a third reagent, a reagent container 222b for housing a fourth reagent, and a reagent container 223 for housing a sheath fluid (diluting fluid). The sample preparation portion 22 is also connected with a compressor, and the respective reagents can be drawn from the corresponding reagent containers 221a, 221b, 222a, 222b, and 223 with the pressure generated by the compressor.

The first reagent is a hemolyzing agent for classifying leucocytes into at least four subclasses. The hemolyzing agent for use contains a cationic surfactant that is said to have a particularly great hemolyzing ability among surfactants. Use of the hemolyzing agent allows erythrocytes to be hemolyzed and the cell membranes of normal leukocytes and abnormal mononuclear leukocytes (atypical lymphocytes, abnormal lymphocytes, and blasts) to be damaged. Accordingly, normal leukocytes and abnormal mononuclear leukocytes are more likely to be stained with a fluorescent dye that will be described below.

"Abnormal lymphocyte" means a mature lymphocyte which is neoplastic. The abnormal lymphocyte appears in a peripheral blood of a patient with diseases such as chronic lymphocytic leukemia and malignant lymphoma. "Atypical lymphocyte" means a lymphocyte which is antigenically-stimulated and altered morphology in response to the stimulation. The atypical lymphocyte appears in a peripheral blood of a patient with diseases such as viral infection and drug allergy.

"Blast" means an immature lymphocyte such as myeloblast and lymphoblast. The myeloblast appears in a peripheral blood of a patient with acute myelocytic leukemia, and the lymphoblast appears in a peripheral blood of a patient with acute lymphatic leukemia.

Here, a quaternary ammonium salt surfactant or a pyridinium salt surfactant is preferable as a cationic surfactant. More specific examples include surfactants having 9 to 30 total carbon atoms as represented by structural formula (I) or (II):

wherein $R_1$ is an alkyl or alkenyl group having 6 to 18 carbon atoms; $R_2$ and $R_3$ each are an alkyl or alkenyl group having 1 to 4 carbon atoms; $R_4$ is an alkyl or alkenyl group having 1 to 4 carbon atoms or a benzyl group; and X is a halogen atom.

$R_1$ is preferably an alkyl or alkenyl group having 6, 8, 10, 12, or 14 carbon atoms, with a linear alkyl group being particularly preferable. More specific examples of $R_1$ include an octyl group, a decyl group, and a dodecyl group. $R_2$ and $R_3$ each are particularly preferably a methyl group, an ethyl group, or a propyl group. $R_4$ is preferably a methyl group, an ethyl group, or a propyl group.

The first reagent may further contain a nonionic surfactant. The nonionic surfactant is preferably a polyoxyethylene-based nonionic surfactant represented by structural formula (III) below:

$$R_1\text{—}R_2\text{—}(CH_2CH_2O)n\text{-H} \quad (III)$$

wherein $R_1$ is an alkyl, alkenyl, or alkynyl group having 8 to 25 carbon atoms; $R_2$ is O,

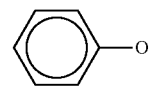

or COO: and n represents an integer of 10 to 50.

The first reagent may contain components other than the cationic surfactants and the nonionic surfactants mentioned above. Examples of such other components that may be contained in the hemolyzing agent include organic acids, buffers, and the like.

Here, as for the organic acids, organic acids that have at least one aromatic ring in the molecule or salts thereof are preferable. More specific examples include benzoic acid, phthalic acid, hippuric acid, salicylic acid, p-aminobenzenesulfonic acid, benzenesulfonic acid, salts thereof, and the like.

Examples of buffers include citric acid salts, HEPES, phosphoric acid salts, and the like. Preferable buffers maintain the pH of the hemolyzing agent at 4.5 to 11.0 and preferably 5.0 to 10.0.

Due to the use of the first reagent, normal leukocytes and abnormal mononuclear leukocytes are more likely to be stained with a fluorescent dye that will be described below, and in addition, normal leukocytes develop a difference in size or other features of lymphocytes, monocytes, eosinophils, and granulocytes other than eosinophils. It is therefore possible based on the fluorescent signal (fluorescence intensity) and the scattered light signal (scattered light intensity) derived from hemocytes to classify normal leukocytes into at least four subclasses and to detect abnormal mononuclear leukocytes.

Moreover, commercially available hemolyzing reagents for leukocyte classification can also be used for the first reagent. An example of a commercially available hemolyzing reagent for leukocyte classification may be a Stomatolyser 4DL manufactured by Sysmex Corporation. The Stomatolyser 4DL is a hemolyzing agent containing the aforementioned cationic surfactant, nonionic surfactant, and organic acid, and having a pH within the aforementioned range.

The second reagent is a reagent for fluorescently staining nucleated cells in a blood sample. A fluorescent dye for staining nucleic acid is contained in the second reagent. Such a dye barely stains erythrocytes that do not have nucleic acid, but stains nucleated hemocytes such as leukocytes having nucleic acid and nucleated erythrocytes. The fluorescent dye capable of staining nucleic acid can be suitably selected according to the light irradiated from a light source.

Specific examples of fluorescent dyes capable of staining nucleic acid include propidium iodide, ethidium bromide, ethidium-acridine heterodimer, ethidium diazide, ethidium homodimer-1, ethidium homodimer-2, ethidium monoazide, trimethylenebis[[3-[[4-[[(3-methylbenzothiazol-3-ium)-2-yl]methylene]-1,4-dihydroquinoline]-1-yl]propyl]dimethylaminium]tetraiodide (TOTO-1), 4-[(3-methylbenzothiazol-2(3H)-ylidene)methyl]-1-[3-(trimethylaminio)propyl]quinolinium diiodide (TO-PRO-1), N,N,N',N'-tetramethyl-N,N'-bis[3-[4-[3-[(3-methylbenzothiazol-3-ium)-2-yl]-2-propenylidene]-1,4-dihydroquinolin-1-yl]propyl]-1,3-propandiaminium tetraiodide (TOTO-3), 2-[3-[[1-[3-(trimethylaminio)propyl]-1,4-dihydroquinolin]-4-ylidene]-1-propenyl]-3-methylbenzothiazol-3-ium diiodide (TO-PRO-3), and fluorescent dyes represented by structural formula (IV) below. Among these examples, the fluorescent dyes represented by structural formula (IV) below are preferable.

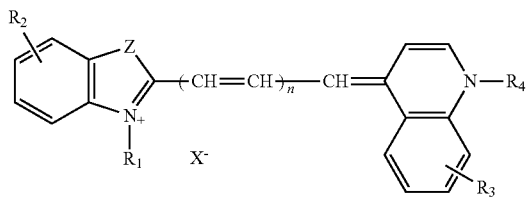

(IV)

In the formula, $R_1$ and $R_4$ each represent a hydrogen atom, an alkyl group, an alkyl group having a hydroxy group, an alkyl group having an ether group, an alkyl group having an ester group, or a benzyl group optionally having a substituent; $R_2$ and $R_3$ each are a hydrogen atom, a hydroxyl group, a halogen, an alkyl group, an alkenyl group, an alkynyl group, or an alkoxy group; Z is a sulfur atom, an oxygen atom, or a carbon atom having a methyl group; n is 0, 1, 2, or 3; and $X^-$ is an anion.

Here, it is preferable that when one of $R_1$ and $R_4$ in structural formula (IV) is an alkyl group having 6 to 18 carbon atoms, the other is a hydrogen atom or an alkyl group having fewer than 6 carbon atoms. The alkyl group having 6 to 18 atoms is preferably an alkyl group having 6, 8, or 10 carbon atoms. Examples of substituents of the benzyl group represented by $R_1$ and $R_4$ include alkyl groups having 1 to 20 carbon atoms, alkenyl groups having 2 to 20 carbon atoms, and alkynyl groups having 2 to 20 carbon atoms, with a methyl group or an ethyl group being particularly preferable. Examples of alkenyl groups represented by $R_2$ and $R_3$ include alkenyl groups having 2 to 20 carbon atoms. Examples of alkoxy groups represented by $R_2$ and $R_3$ include alkoxy groups having 1 to 20 carbon atoms, with a methoxy group or an ethoxy group being particularly preferable. Examples of anions represented by $X^-$ include $F^-$, $Cl^-$, $Br^-$, $I^-$, and like halogen ions, $CF_3SO_3^-$, $BE_4^-$, and the like.

The concentration of fluorescent dye capable of staining nucleic acid in the second reagent can be suitably determined according to the kind of fluorescent dye. For example, the concentration of fluorescent dye represented by structural formula (IV) is preferably 0.2 to 0.6 pg/µL and particularly preferably 0.3 to 0.5 pg/µL. The second reagent may contain one or two or more fluorescent dyes capable of staining nucleic acid.

Moreover, commercially available staining reagents for leukocyte classification can also be used for the second reagent. An example of a commercially available staining reagent for leukocyte classification may be a Stomatolyser 4DS manufactured by Sysmex Corporation. The Stomatolyser 4DS is a staining reagent containing a fluorescent dye represented by structural formula (IV) above.

The sheath fluid is a fluid supplied to a sheath flow cell that will be described below. The sheath fluid is also used as a diluting fluid. An example of the sheath fluid may be a Cellpack (II) manufactured by Sysmex Corporation.

The third reagent is a hemolyzing agent for distinguishably detecting an abnormal lymphocyte, an atypical lymphocyte, and a blast. Hemolyzing agents that contain a nonionic surfactant and do not substantially contain a cationic surfactant can be used for the third reagent. Use of the hemolyzing agent allows erythrocytes to be hemolyzed and the cell membranes of normal leukocytes and abnormal mononuclear leukocytes to be damaged. Accordingly, normal leukocytes and abnormal mononuclear leukocytes are more likely to be stained with a fluorescent dye that will be described below.

"Abnormal lymphocyte" is a neoplastic mature lymphocyte. This abnormal lymphocyte appears in a peripheral blood of a patient who has a disease such as a chronic lymphocytic leukemia and a lymphatic malignancy. "Atypical lymphocyte" is a lymphocyte activated by antigen stimulation and is a lymphocyte whose shape changed in response to the stimulation. This atypical lymphocyte appears in a peripheral blood of a patient who has a disease such as viral infection and drug allergy. The atypical lymphocyte is a reactive abnormal mononuclear leukocyte.

"Blast" is a neoplastic immature mononuclear cell which is an immature leukocyte such as myeloblast and lymphoblast. The myeloblast appears in a peripheral blood of a patient with acute myelocytic leukemia, and the lymphoblast appears in a peripheral blood of a patient with acute lymphatic leukemia. A neoplastic abnormal mononuclear cell including the abnormal lymphocyte and the blast is an abnormal mononuclear cell caused by a tumor of the hematopoietic organ.

Here, the nonionic surfactant is preferably a polyoxyethylene-based nonionic surfactant. Specific examples of polyoxyethylene-based nonionic surfactants include those represented by structural formula (V) below:

$$R_1-R_2-(CH_2CH_2O)n-H \qquad (V)$$

wherein $R_1$ an alkyl, alkenyl, or alkynyl group having 9 to 25 carbon atoms; $R_2$ is —O—, —COO—, or:

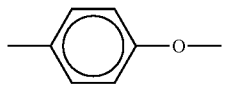

and n is an integer of 10 to 40.

Specific examples of surfactants represented by structural formula (V) above include polyoxyethylene (15) oleyl ether, polyoxyethylene (15) cetyl ether, polyoxyethylene (16) oleyl ether, polyoxyethylene (20) oleyl ether, polyoxyethylene (20) lauryl ether, polyoxyethylene (20) stearyl ether, polyoxyethylene (20) cetyl ether, and the like, with polyoxyethylene (20) oleyl ether being preferable. The third reagent may contain one or more surfactants.

The concentration of surfactant contained in the third reagent can be suitably selected according to the kind of surfactant, the osmotic pressure of the hemolyzing agent, and like factors. For example, when the surfactant is polyoxyethylene oleyl ether, the concentration of surfactant contained in the third reagent is 0.5 to 50.0 g/L and preferably 1.0 to 20.0 g/L.

The third reagent may contain in addition to the nonionic surfactant a solubilizing agent to sufficiently shrink the hemolyzed erythrocytes so that the hemolyzed erythrocytes form a ghost population that does not adversely affect measurement. Examples of solubilizing agents that may be contained in the third reagent include sarcosine derivatives, cholic acid derivatives, methylglucanamide, n-octyl-β-glucoside, sucrose monocaprate, N-formylmethylleucylalanine, and the like, with sarcosine derivatives being particularly preferable. The third reagent may contain one or two or more solubilizing agents.

Examples of sarcosine derivatives include compounds represented by structural formula (VI) below or salts thereof:

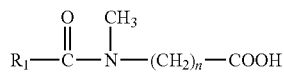

wherein $R_1$ is a C10-22 alkyl group, and n is 1 to 5. Specific examples of sarcosine derivatives include sodium N-lauroyl-sarcosinate, sodium lauroyl methyl β-alanine, lauroyl sarcosine, and the like, with sodium N-lauroylsarcosinate being particularly preferable.

Examples of cholic acid derivatives include compounds represented by structural formula (VII) below or salts thereof:

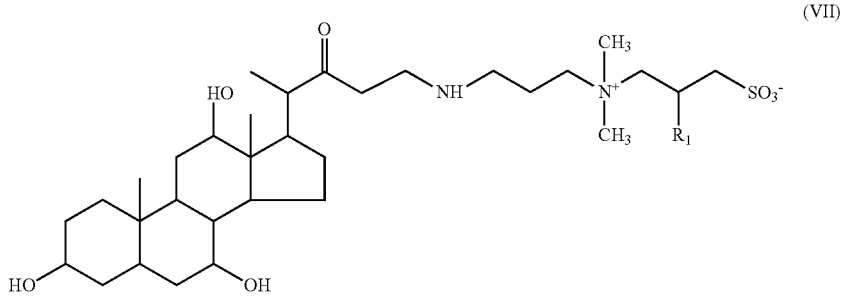

wherein $R_1$ is a hydrogen atom or a hydroxyl group. Specific examples of cholic acid derivatives include CHAPS (3-[(3-cholamidopropyl)dimethylammonio]-1-propanesulfonate), CHAPSO ([(3-cholamidopropyl)dimethylammonio]-2-hydroxy-1-propanesulfonate), and the like.

Examples of methylglucanamides include compounds represented by structural formula (VIII) below:

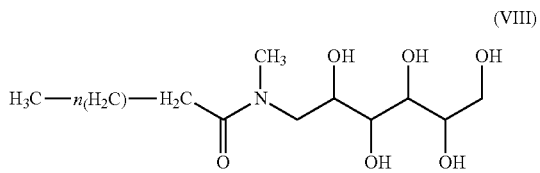

wherein n is 5 to 7. Specific examples of methylglucanamides include MEGA8 (octanoyl-N-methylglucamide), MEGA9 (nonanoyl-N-methylglucamide), MEGA10 (decanoyl-N-methylglucamide), and the like.

The concentration of solubilizing agent contained in the third reagent may be suitably selected according to the kind of solubilizing agent used. For example, when a sarcosine derivative is used as a solubilizing agent, the concentration of solubilizing agent contained in the third reagent is 0.05 to 3.0 g/L and preferably 0.1 to 1.0 g/L. When a cholic acid derivative is used, the concentration of solubilizing agent contained in the third reagent is 0.1 to 10.0 g/L and preferably 0.2 to 2.0 g/L. When a methylglucanamide is used, the concentration of solubilizing agent contained in the third reagent is 1.0 to 8.0 g/L and preferably 2.0 to 6.0 g/L. When n-octyl β-glucoside, sucrose monocaprate or N-formylmethylleucylalanine is used, the concentration of solubilizing agent contained in the third reagent is 0.01 to 50.0 g/L and preferably 0.05 to 30.0 g/L.

The pH of the third reagent is preferably 5.0 to 9.0, more preferably 6.5 to 7.5, and even more preferably 6.8 to 7.3. The pH of the fourth reagent can be controlled with a buffer or a pH adjustor. Examples of buffers include Good's buffers such as HEPES, MOPS (3-morpholinopropanesulfonic acid) and MOPSO (2-Hydroxy-3-morpholinopropanesulfonic acid), phosphate buffers, and the like. Examples of pH adjustors include sodium hydroxide, hydrochloric acid, and the like.

The osmotic pressure of the third reagent can be suitably determined according to the kind of surfactant described above and the concentration thereof in the third reagent. A specific example of the osmotic pressure of the third reagent may be 10 to 600 mOsm/kg. The osmotic pressure of the third reagent may be controlled by adding sugar, amino acid, sodium chloride, or the like to the third reagent. Specific examples of sugars include monosaccharides, polysaccharides, sugar alcohols, and the like. Glucose and fructose are preferable as monosaccharides. Arabinose is preferable as a polysaccharide. Xylitol, sorbitol, mannitol, and ribitol are preferable as sugar alcohols. A sugar to be added to the third reagent is preferably a sugar alcohol and particularly preferably xylitol. When xylitol is added to the third reagent, the concentration of xylitol in the third reagent is preferably 1.0 to 75.0 g/L and particularly preferably 20.0 to 50.0 g/L. Specific examples of amino acids include valine, proline, glycine, alanine, and the like, with glycine and alanine being particularly preferable. When glycine is added to the third reagent, the concentration of glycine in the third reagent is preferably 1.0 to 50.0 g/L and particularly preferably 10.0 to 30.0 g/L.

The electric conductivity of the third reagent is preferably 0.01 to 3 mS/cm and particularly preferably 0.1 to 2 mS/cm. In addition, a chelating agent, a preservative, or the like may be added to the third reagent. Examples of chelating agents include EDTA-2K, EDTA-3Na, and the like. Examples of preservatives include Proxel GXL (manufactured by Avecia), Material TKM-A (API Corporation), and the like.

Due to the use of the third reagent, normal leukocytes and abnormal mononuclear leukocytes are more likely to be stained with a fluorescent dye that will be described below, and in addition, abnormal mononuclear leukocytes develop a difference in size or other features of abnormal lymphocytes, atypical lymphocytes, and blasts. It is therefore possible based on the fluorescent signal (fluorescence intensity) and the scattered light signal (scattered light intensity) derived from hemocytes to distinguishably detect abnormal lymphocytes, atypical lymphocytes, and blasts in abnormal mononuclear leukocytes.

The fourth reagent is a reagent for fluorescently staining nucleated cells in a blood sample. A fluorescent dye capable of staining nucleic acid is contained in the fourth reagent. The fluorescent dye is not particularly limited as long as it is capable of fluorescently staining nucleic acid. Such a dye barely stains erythrocytes that do not have nucleic acid, but stains nucleated hemocytes such as abnormal lymphocytes having nucleic acid. The fluorescent dye capable of staining nucleic acid can be suitably selected according to the light irradiated from a light source. Specific examples of fluorescent dyes capable of staining nucleic acid include propidium iodide, ethidium bromide, ethidium-acridine heterodimer, ethidium diazide, ethidium homodimer-1, ethidium homodimer-2, ethidium monoazide, trimethylenebis[[3-[[4-[[(3-methylbenzothiazol-3-ium)-2-yl]methylene]-1,4-dihydroquinoline]-1-yl]propyl]dimethylaminium]tetraiodide (TOTO-1), 4-[(3-methylbenzothiazol-2(3H)-ylidene)methyl]-1-[3-(trimethylaminio)propyl]quinolinium diiodide (TO-PRO-1), N,N,N',N'-tetramethyl-N,N'-bis[3-[4-[3-[(3-methylbenzothiazol-3-ium)-2-yl]-2-propenylidene]-1,4-dihydroquinolin-1-yl]propyl]-1,3-propandiaminium tetraiodide (TOTO-3), 2-[3-[[1-[3-(trimethylaminio)propyl]-1,4-dihydroquinolin]-4-ylidene]-1-propenyl]-3-methylbenzothiazol-3-ium diiodide (TO-PRO-3), and fluorescent dyes represented by structural formulas (IX) to (XXII) below.

Structural Formula (IX)

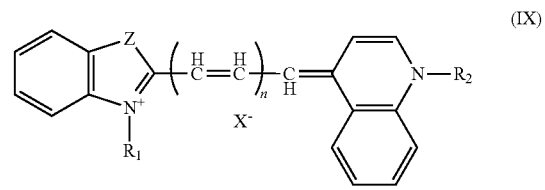

In the formula, $R_1$ and $R_2$ each are a lower alkyl group; n is 1 or 2; X— is an anion; and Z is a sulfur atom, an oxygen atom, or a carbon atom substituted with a lower alkyl group.

In structural formula (IX), the lower alkyl group is a linear or branched alkyl group having 1 to 6 carbon atoms. Specific examples of lower alkyl groups include a methyl group, an ethyl group, a propyl group, a butyl group, an iso-butyl group, a sec-butyl group, a tert-butyl group, a pentyl group, a hexyl group, and the like, with a methyl group and an ethyl group being preferable. Z is preferably a sulfur atom. Examples of anions represented by $X^-$ include halogen ions (fluorine, chlorine, bromine, and iodine ions), boron halide ions ($BF_4^-$, $BCl_4^-$, $BBr_4^-$, and the like), phosphorus compound ions, halogen oxoacid ions, fluorosulfuric acid ions, methylsulfuric acid ions, ions of tetraphenylboron compounds having a haloaromatic ring or an alkyl group having a halogen as a substituent, and the like, with an iodine ion being preferable.

Among the fluorescent dyes represented by structural formula (IX), a particularly preferable fluorescent dye capable of staining nucleic acid is NK-321 represented by structural formula (X) below:

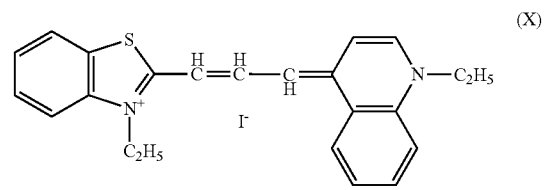 [SMILES: CCN1C=CC(=CC=Cc2sc3ccccc3[n+]2CC)c2ccccc21 ; [I-]]

Structural formula (XI)

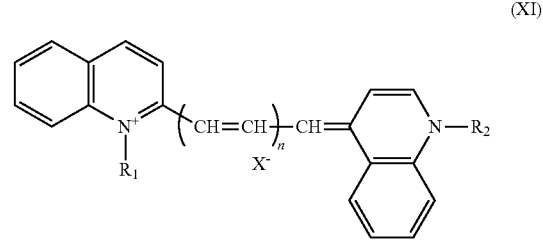

In the formula, $R_1$ and $R_2$ each are a lower alkyl group; n is 1 or 2; and $X^-$ is an anion.

The lower alkyl group and the anion $X^-$ in structural formula (XI) are the same as those in structural formula (IX).

Among the fluorescent dyes represented by structural formula (XI), a particularly preferable fluorescent dye capable of staining nucleic acid is represented by structural formula (XII) below:

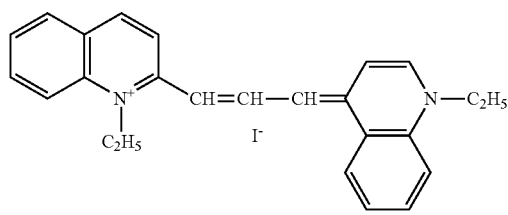

(XII)

Structural Formula (XIII)

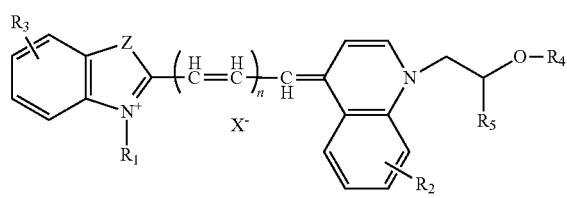

(XIII)

In the formula, $R_1$ is a hydrogen atom or a lower alkyl group; $R_2$ and $R_3$ each are a hydrogen atom, a lower alkyl group, or a lower alkoxy group; $R_4$ is a hydrogen atom, an acyl group, or a lower alkyl group; $R_5$ is a hydrogen atom or a lower alkyl group that may be substituted; Z is a sulfur atom, an oxygen atom, or a carbon atom substituted with a lower alkyl group; n is 1 or 2; and $X^-$ is an anion.

The lower alkyl group and the anion represented by $X^-$ in structural formula (XIII) are the same as those in structural formula (IX). The lower alkoxy group refers to an alkoxy group having 1 to 6 carbon atoms. Specific examples of lower alkoxy groups include a methoxy group, an ethoxy group, a propoxy group, and the like, with a methoxy group and an ethoxy group being particularly preferable. The acyl group is preferably an acyl group derived from an aliphatic carboxylic acid. Specific examples of acyl groups include an acetyl group, a propionyl group, and the like, with an acetyl group being particularly preferable. Examples of substituents of the lower alkyl group that may be substituted include a hydroxyl group and halogen atoms (fluorine, chlorine, bromine, and iodine). The lower alkyl group that may be substituted may be substituted by 1 to 3 substituents. It is particularly preferable that the lower alkyl group that may be substituted is a lower alkyl group substituted with one hydroxyl group. Z is preferably a sulfur atom and $X^-$ is preferably a bromine ion or $BF_4^-$.

Among the fluorescent dyes represented by structural formula (XIII), particularly preferable fluorescent dyes capable of staining nucleic acid are represented by any of the three structural formulas (XIV) to (XVI) below:

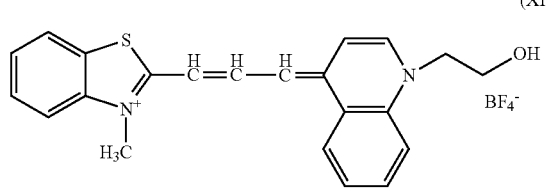

(XIV)

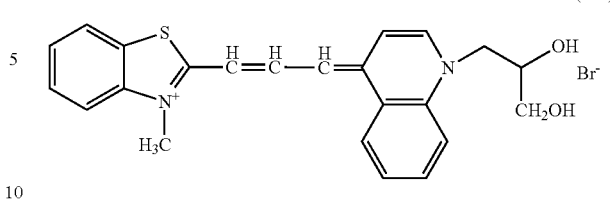

(XV)

(XVI)

Structural formula (XVII)

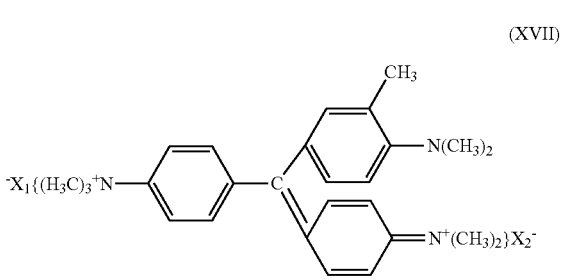

(XVII)

In the formula, $X_1$ and $X_2$ are independently Cl or I.

Structural formula (XVIII)

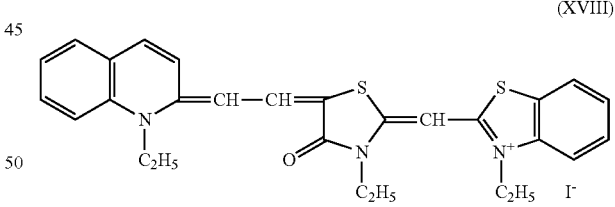

(XVIII)

Structural Formula (XIX) (NK-1570)

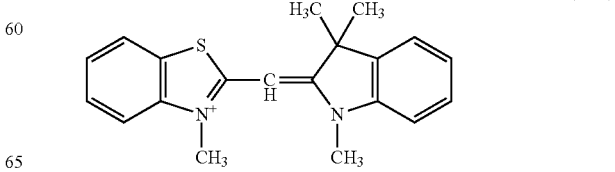

(XIX)

Structural formula (XX) (NK-1049)

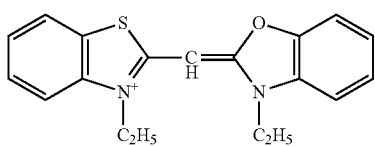

(XX)

Structural Formula (XXI) (NK-98)

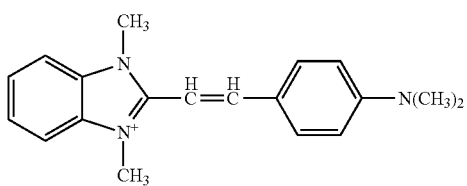

(XXI)

Structural Formula (XXII) (NK-141)

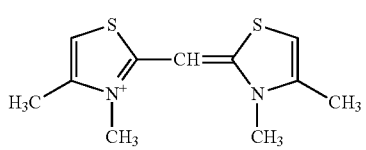

(XXII)

Among the fluorescent dyes capable of staining nucleic acid, a particularly preferable fluorescent dye contained in the fourth reagent is NK-321 represented by the structural formula (XXIII) below:

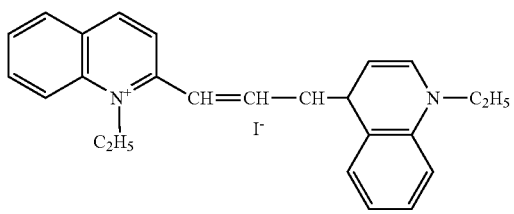

(XXIII)

The concentration of fluorescent dye capable of staining nucleic acid in the fourth reagent is preferably 10 to 500 mg/L and particularly preferably 30 to 100 mg/L. The fourth reagent may contain one or two or more fluorescent dyes capable of staining nucleic acid.

The detection portion 23 includes an optical detector D that can conduct a first measurement and a second measurement. In the first measurement, leukocytes (normal leukocytes) present in a blood specimen are classified into four subclasses: LYMPH (lymphocytes); EO (eosinophils); a hemocyte group consisting of NEUT (neutrophils) and BASO (basophils); and MONO (monocytes). In the first measurement, a measurement sample (first measurement sample) obtained by mixing the blood specimen, the first reagent, and the second reagent is supplied to the optical detector D, and optical information (fluorescence intensity, forward scattered light intensity, and side scattered light intensity) is detected by the optical detector D at this time. The optical information obtained by the first measurement is supplied to the information processing unit 5, and thereby the normal leukocytes contained in the blood specimen are classified into the four subclasses. As will be described later, the information processing unit 5 can detect abnormal mononuclear leukocytes (a group consisting of abnormal lymphocytes, atypical lymphocytes, and blasts) in the blood specimen based on the optical information obtained by the first measurement.

In the second measurement, abnormal lymphocytes and blasts contained in the blood specimen are detected. In the second measurement, a measurement sample (second measurement sample) obtained by mixing the blood specimen, the third reagent, and the fourth reagent is supplied to the optical detector D, and optical information (fluorescence intensity, forward scattered light intensity, and side scattered light intensity) is detected by the optical detector D at this time. The optical information obtained by the second measurement is supplied to the information processing unit 5, thereby identifying whether the abnormal mononuclear leukocytes contained in the blood specimen that have been detected by the first measurement are abnormal lymphocytes, atypical lymphocytes, or blasts.

Figure 3:
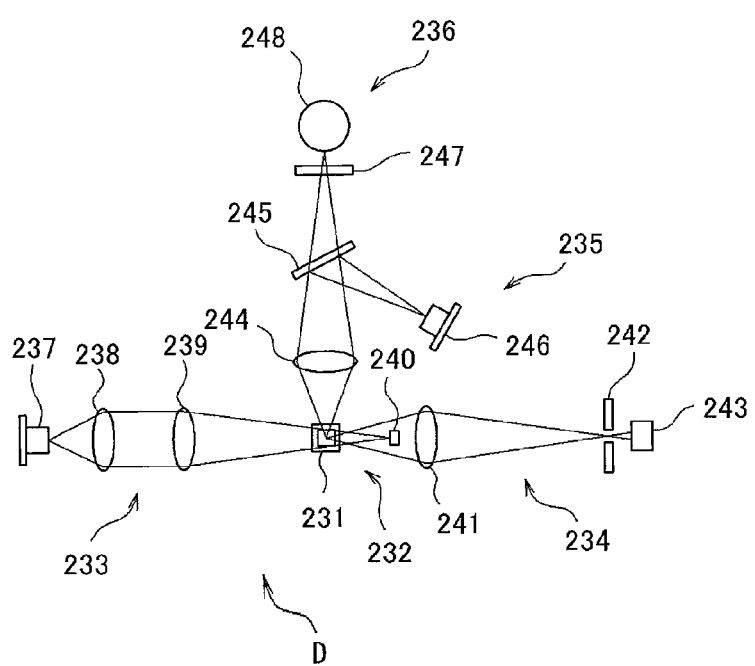
FIG. 3 is a schematic diagram showing the configuration outline of an optical detector.

FIG. 3 shows a configuration outline of the optical detector D. The optical detector D feeds the measurement samples and the sheath fluid into a flow cell 231 to generate a liquid current in the flow cell 231, and measures the hemocytes contained in the liquid current flossing through the flow cell 231 by irradiating semiconductor laser light onto the hemocytes. The optical detector D includes a sheath flows system 232, a beam spot formation system 233, a forward scattered light receiving system 234, a side scattered light receiving system 235, and a fluorescence light receiving system 236.

The sheath flows system 232 is configured to cause the measurement samples to flow through the flow cell 231 in such a state where the measurement samples are each enclosed in the sheath fluid. The beam spot formation system 233 is configured to allow light irradiated from a semiconductor laser 237 to be irradiated onto the flow cell 231 through a collimator lens 238 and a condenser lens 239. Further, the beam spot formation system 233 includes a beam stopper 240.

The forward scattered light receiving system 234 is configured to focus forward scattered light with a forward focusing lens 241, and receive the light that has passed through a pinhole 242 with a photodiode (forward scattered light receiving portion) 243.

The side scattered light receiving system 235 is configured to focus side scattered light with a side focusing lens 244, reflect a portion of the light at a dichroic mirror 245, and receive the reflected light with a photodiode (side scattered light receiving portion) 246.

Light scattering is a phenomenon that occurs when light changes the direction of its movement due the presence of particles such as hemocytes in the movement direction as impediments. Information relating to the size and the material of the particles can be obtained by detecting such scattered light. In particular, information relating to the size of the particles (hemocytes) can be obtained from forward scattered light. Meanwhile, information about the interior of the particles can be obtained from side scattered light. When laser light is irradiated onto hemocyte particles, the intensity of side scattered light is dependent on the complexity of the cell interior (the shape, size, density, and the granular amount of the nucleus). Therefore, the intensity of these scattered light beams can be utilized for classification of leukocytes, detection of abnormal mononuclear leukocytes, detection of blasts, and other measurements.

The fluorescence light receiving system 236 is configured to allow the light that has transmitted through the dichroic mirror 245 to further transmit through a spectral filter 247, and receive the transmitted light with an avalanche photodiode (fluorescence light receiving portion) 248.

When light is irradiated onto a hemocyte that has been stained by a fluorescent substance, the hemocyte emits light having a wavelength longer than the wavelength of the irradiated light. The intensity of fluorescence is increased if the hemocyte has been stained well, and information relating to the staining degree of the hemocyte can be obtained by measuring the fluorescence intensity. Accordingly, the difference in (side) fluorescence intensity can be utilized for classification of leukocytes, detection of abnormal mononuclear leukocytes, detection of abnormal lymphocytes, detection of blasts, and the like.

Referring back to FIG. 2, the configuration of the specimen container carrying portion 25 will now be described next. The specimen container carrying portion 25 includes a hand portion 25a that can grip the specimen container T. The hand portion 25a includes a pair of gripping members arranged facing each other, and can move these gripping members toward and away from each other. The specimen container T can be gripped by the gripping members by moving the gripping members toward each other with the specimen container T interposed therebetween. Further, the specimen container carrying portion 25 can move the hand portion 25a in the up-down direction and the front-back direction (Y direction), and also can oscillate the hand portion 25a. This allows the specimen container T housed in the sample rack L and located at the specimen supply position 43a to be gripped by the hand portion 25a. In this state, the hand portion 25a is moved upward to pull out the specimen container T from the sample rack L. Then, the specimen in the specimen container T can be agitated by oscillating the hand portion 25a.

The specimen container carrying portion 25 also includes a specimen container setting portion 25b having a hole into which the specimen container T can be inserted. After completion of agitation, the specimen container T gripped by the hand portion 25a described above is moved such that the gripped specimen container T is inserted into the hole of the specimen container setting portion 25b. Then, the gripping members are moved away from each other, thereby releasing the specimen container T from the hand portion 25a and setting the specimen container T in the specimen container setting portion 25b. The specimen container setting portion 25b can be moved horizontally in Y1 and Y2 directions in FIG. 2 by the power of a stepping motor.

A bar code reading portion 26 is provided inside the measurement unit 2. The specimen container setting portion 25b can be moved to a bar code reading position 26a in the vicinity of the bar code reading portion 26 and to the suction position where the specimen is sucked by the specimen suction portion 21. When the specimen container setting portion 25b is moved to the bar code reading position 26a, the bar code of the specimen is read by the bar code reading portion 26. When the specimen container setting portion 25b is moved to the suction position, the specimen is sucked by the specimen suction portion 21 from the specimen container T that has been set.

Configuration of Information Processing Unit

Figure 4:
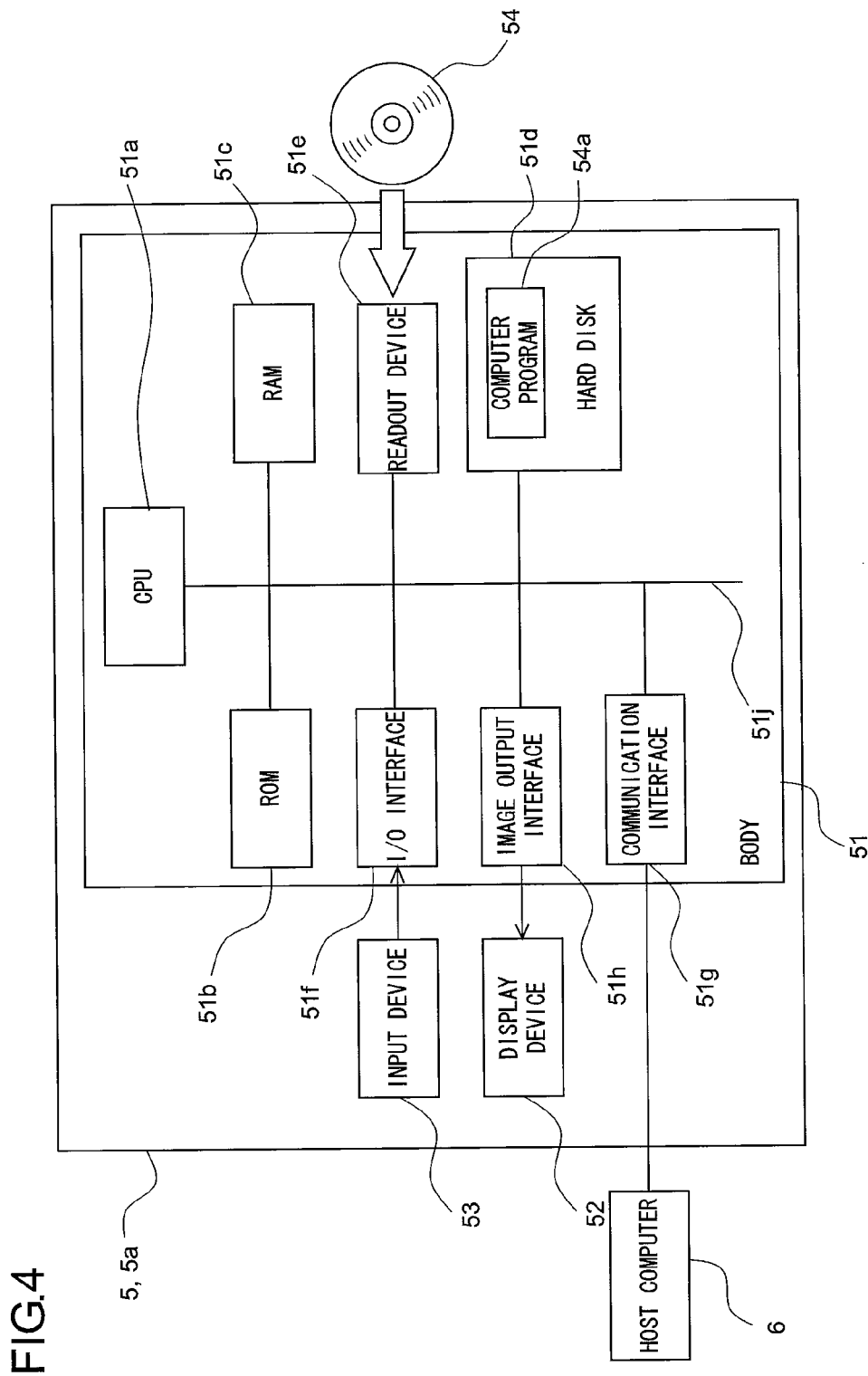
FIG. 4 is a block diagram showing the configuration of an information processing unit according to the embodiment.

Next, the configuration of the information processing unit 5 will now be described. The information processing unit 5 is configured by a computer. FIG. 4 is a block diagram showing the configuration of the information processing unit 5. The information processing unit 5 can be implemented by a computer 5a. As shown in FIG. 4, the computer 5a includes a body 51, a display device 52, and an input device 53. The body 51 includes a CPU 51a, a ROM 51b, a RAM 51c, a hard disk 51d, a readout device 51e, an input/output interface 51f, a communication interface 51g, and an image output interface 51h. The CPU 51a, the ROM 51b, the RAM 51c, the hard disk 51d, the readout device 51e, the input/output interface 51f, the communication interface 51g, and the image output interface 51h are connected by a bus 51j.

The CPU 51a can execute a computer program loaded into the RAM 51c. The computer 5a functions as the information processing unit 5 by the CPU 51a executing a computer program 54a for blood analysis and control of the measurement unit 2 and the specimen carrying unit 4 as will be described later.

Various computer programs, including, for example, an operating system and application programs, for being executed by the CPU 51a, and the data used for execution of such computer programs are installed in the hard disk 51. The computer program 54a for enabling the CPU 51a to execute processing described later is also installed in the hard disk 51d. The computer program 54a is an event-driven computer program.

The readout device 51e is configured by a flexible disk drive, a CD-ROM drive, a DVD-ROM drive, or the like, and can read out the computer programs or data recorded in a portable recording medium 54. The computer program 54a for enabling the computer to function as the information processing unit 5 is stored in the portable recording medium 54. The computer 5a can read out the computer program 54a from the portable recording medium 54, and install the computer program 54a in the hard disk 51d.

For example, a multitasking operating system such as Windows (registered trademark) manufactured and sold by Microsoft Corporation, US is installed in the hard disk 51d. The following description is given assuming that the computer program 54a according to this embodiment runs on that operating system.

The input/output interface 51f is configured, for example, by a serial interface such as USB, IEEE1394, or RS-232C, a parallel interface such as SCSI, IDE, or IEEE1284, and an analog interface made up of a D/A converter, an A/D converter, and the like. An input device 53 made up of a keyboard and a mouse is connected to the input/output interface 51f, and the user can input data into the computer 5a using the input device 53. Further, the input/output interface 51f is connected to the measurement unit 2 and the specimen carrying unit 4. This enables the information processing unit 5 to control each of the measurement unit 2 and the specimen carrying unit 4.

The communication interface 51g is an Ethernet (registered trademark) interface. The communication interface 51g is connected to a host computer 6 via a LAN (see FIG. 2). The computer 5a can transmit and receive data via the communication interface 51g to and from the host computer 6 connected to the LAN using a predetermined communications protocol.

Measuring Operation of Blood Analyzer

Figure 5:
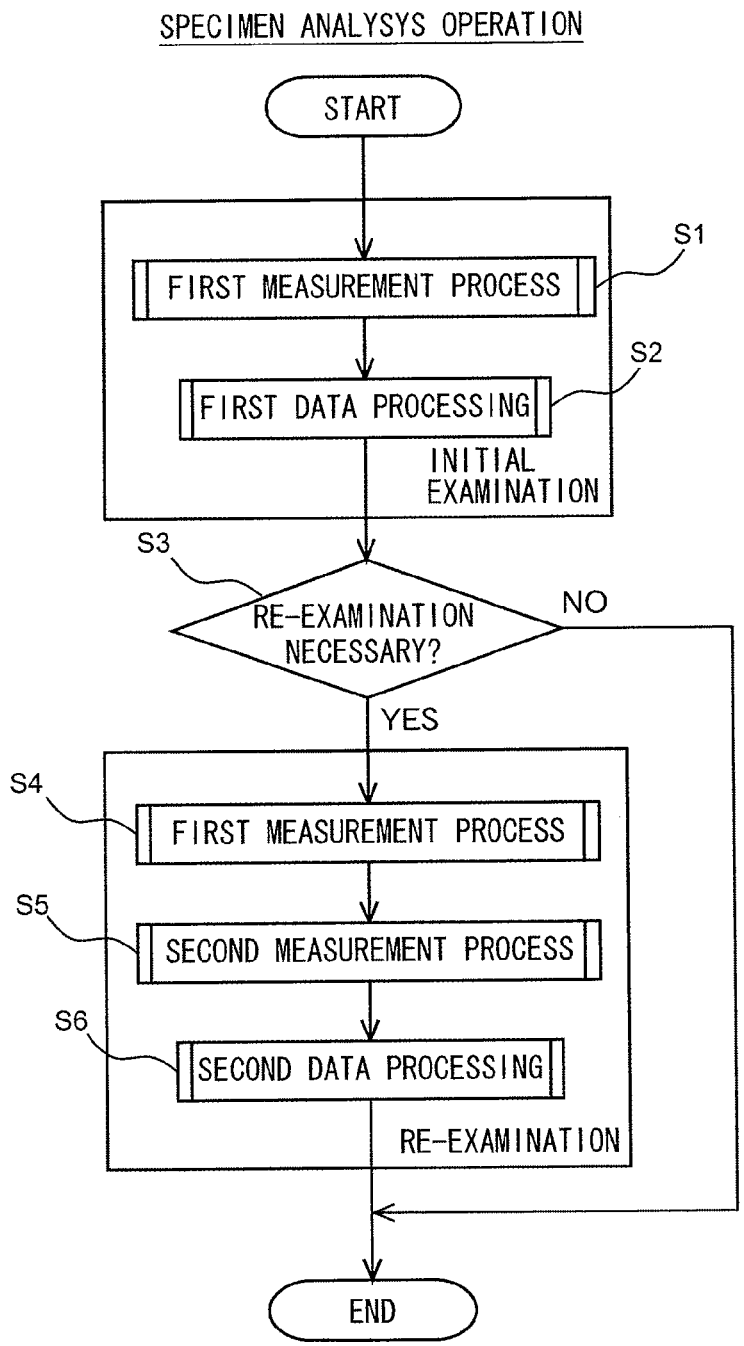
FIG. 5 is a flowchart illustrating the procedure of a specimen analysis operation performed by the blood analyzer according to the embodiment.

In the following, the operation of the blood analyzer 1 according to this embodiment will now be described. The blood analyzer 1 performs a specimen analysis operation as described below. FIG. 5 is a flowchart illustrating the procedure of the specimen analysis operation performed by the blood analyzer 1.

As shown in FIG. 5, in the specimen analysis operation, the initial examination (the first measurement) of a specimen is conducted first. The initial examination includes a first measurement process (step S1) in which a first measurement sample is measured by the measurement unit 2 and first data processing (step S2) in which the measurement data obtained in the first measurement process is subjected to analysis processing performed by the information processing unit 5.

First, the sample rack L holding the specimen container T is placed on the specimen carrying unit 4 by the operator. The sample rack L is carried by the specimen carrying unit 4, and the specimen container T housing a specimen to be measured is positioned in the specimen supply position 43a. Next, the specimen container T is gripped by the hand portion 25a of the measurement unit 2, and the specimen container T is taken out from the sample rack L. The hand portion 25a then causes oscillating movement, and thereby the specimen inside the specimen container T is agitated. Next, the specimen container T is inserted into the specimen container setting portion 25b, and the specimen container setting portion 25b is moved in the Y direction. After the bar code of the specimen is read by the bar code reading portion 26, the specimen container T reaches the suction position. Then, a first measurement process described below is performed.

First Measurement Process

The first measurement process will now be described first. In the first measurement process, the blood analyzer 1 mixes a whole blood specimen (17 µL), a first reagent (1 mL), and a second reagent (20 µL) to prepare a first measurement sample, and measures the first measurement sample by flow cytometry using the optical detector D. Here, the above-described Stomatolyser 4DL is used as the first reagent, and the above-described Stomatolyser 4DS is used as the second reagent.

Figure 6:
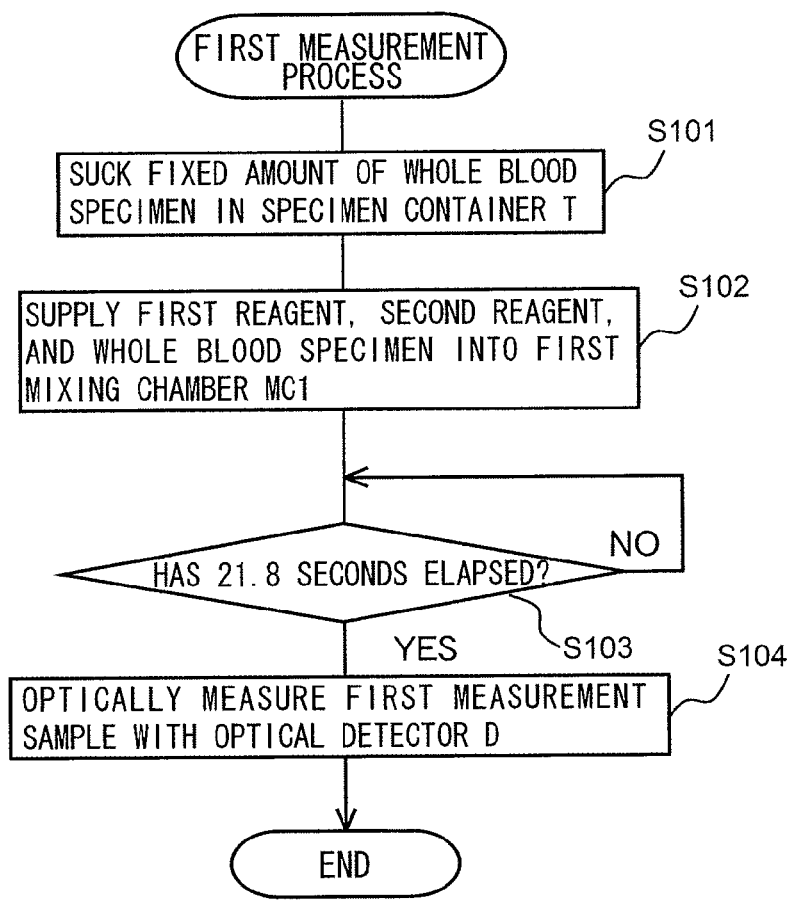
FIG. 6 is a flowchart illustrating the procedure of operation in a first measurement process performed by the blood analyzer according to the embodiment.

FIG. 6 is a flowchart illustrating the procedure of operation performed by the blood analyzer 1 in the first measurement process. First, the CPU 51a controls the specimen suction portion 21 to suck a fixed amount of the whole blood specimen in the specimen container T with the suction tube 211 (step S101). Specifically, in the processing of step S101, the suction tube 211 is inserted into the specimen container T, and a fixed amount (80.0 µL) of the whole blood specimen is sucked by driving the syringe pump.

Next, the CPU 51a controls the measurement unit 2 to supply, to the first mixing chamber MC1, the first reagent (1 mL) from the reagent container 221a, the second reagent (20 µL) from the reagent container 221b, and the whole blood specimen (17 µL) from the suction tube 211 (step S102).

Next, the CPU 51a waits 21.8 seconds and determines whether 21.8 seconds have elapsed since the supply of the first reagent, the second reagent and the whole blood specimen to the first mixing chamber MC1 (step S103). Here, the first mixing chamber MC1 has been heated to 41° C. by the heater. Thus, the mixed solution of the first reagent, the second reagent and the blood specimen is heated at 41° C. for 21.8 seconds to prepare the first measurement sample.

Then, optical measurement is conducted on the first measurement sample with the optical detector D (step S104). Specifically, in the processing of step S104, the first measurement sample and the sheath fluid are simultaneously supplied to the flow cell 231 of the optical detector D. At that time, forward scattered light is received by the photodiode 243, and side scattered light is received by the photodiode 246, and fluorescence light is received by the avalanche photodiode 248. Output signals (analog signals) output from these various light-receiving elements of the optical detector D are converted into digital signals by an A/D converter, and then converted into first measurement data that is digital data through predetermined signal processing. The first measurement data is transmitted to the information processing unit 5. In this signal processing, a forward scattered light signal (forward scattered light intensity), a side scattered light signal (side scattered light intensity), and a fluorescence signal (fluorescence intensity) are obtained as feature parameters contained in the first measurement data. This completes the first measurement process. As will be described later, the CPU 51a of the information processing unit 5 performs predetermined analysis processing on the first measurement data to generate analysis result data containing numeric data for NEUT, LYMPH, EO, BASO, MONO, WBC, and the like, and stores the analysis result data in the hard disk 51d.

First Data Processing

Figure 7:
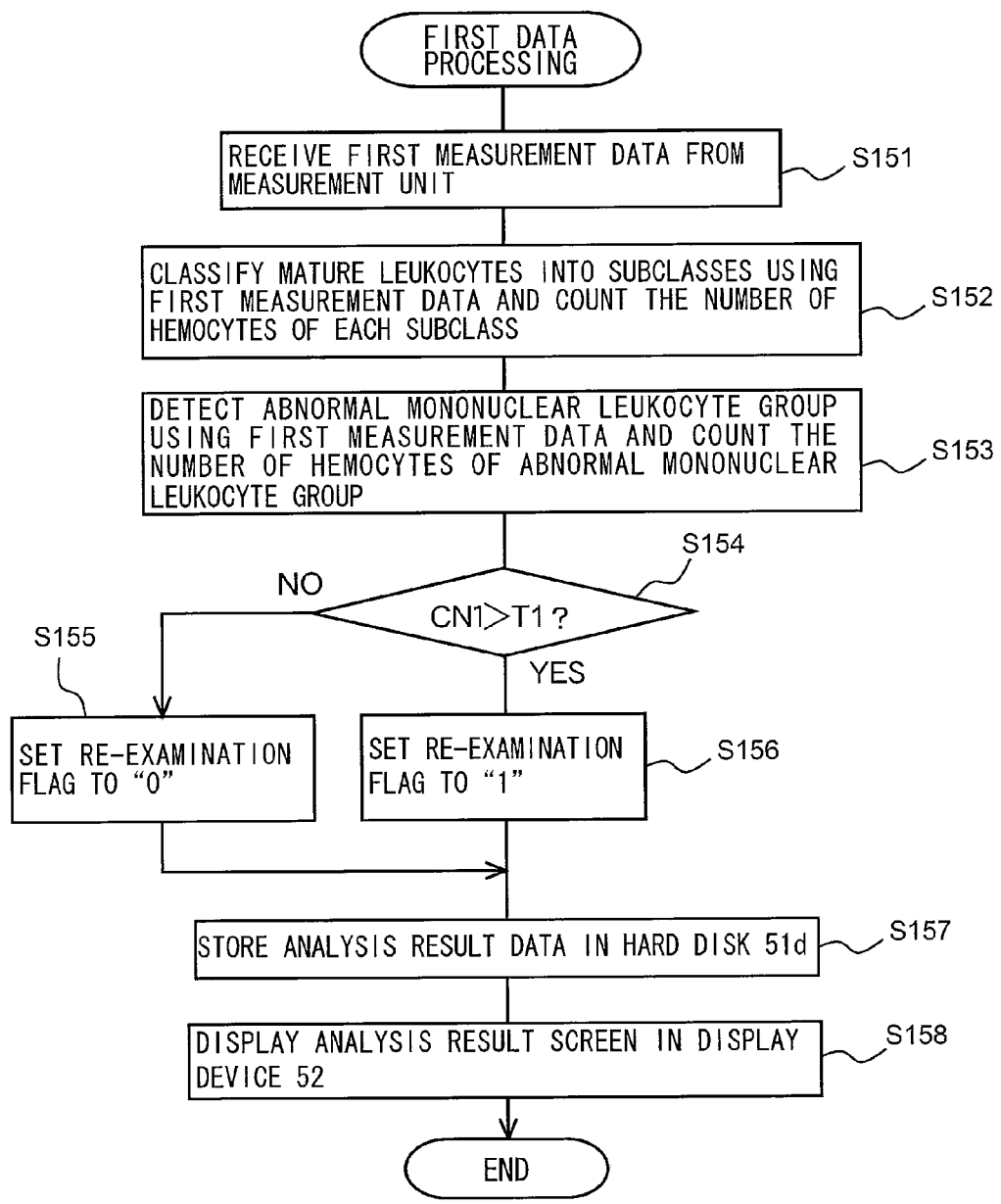
FIG. 7 is a flowchart illustrating the procedure of first data processing performed by the blood analyzer according to the embodiment.

Next, the first data processing will now be described. FIG. 7 is a flowchart showing the procedure of the first data processing performed by the blood analyzer according to this embodiment. The information processing unit 5 of the blood analyzer 1 receives the first measurement data from the measurement unit 2 (step S151). The computer program 54a, which is executed by the CPU 51a, is an event-driven program, and the processing of step S152 is invoked upon occurrence of an event of receiving the first measurement data.

The CPU 51a classifies the normal leukocytes into a plurality of subclasses using the first measurement data, and counts the number of hemocytes belonging to each of the subclasses (step S152). Further, the CPU 51a detects a cell group of abnormal mononuclear leukocytes (hereinafter, referred to as an "abnormal mononuclear leukocyte group") using the first measurement data, and counts the number of hemocytes CN1 contained in the detected abnormal mononuclear leukocyte group (step S153).

Figure 8:
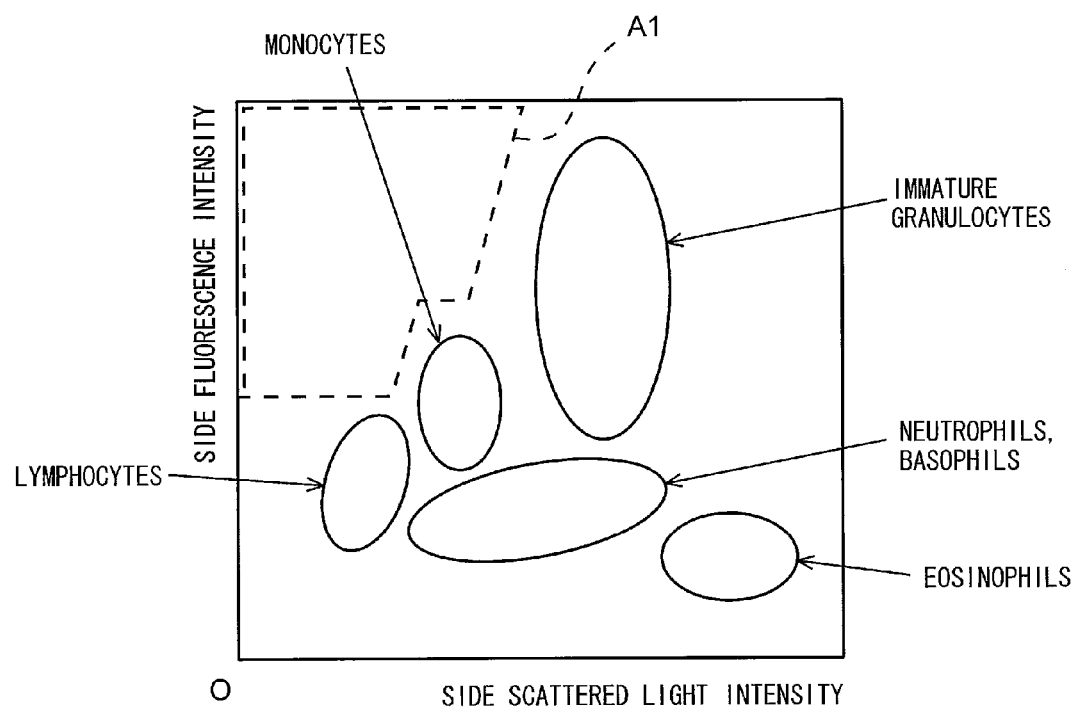
FIG. 8 is a scattergram of side scattered light intensity and fluorescence intensity in first measurement data.

The processing of step S152 and S153 will now be described in detail. FIG. 8 is a scattergram of side scattered light intensity and fluorescence intensity in the first measurement data. A cluster of immature granulocytes, a cluster of eosinophils, a cluster of a hemocyte group consisting of neutrophils and basophils, a cluster of lymphocytes, and a cluster of monocytes appear in the scattergram of side scattered light intensity and fluorescence intensity in the first measurement data shown in FIG. 8. As can be seen from the scattergram in FIG. 8, normal leukocytes can be classified into eosinophils, a hemocyte group consisting of neutrophils and basophils, lymphocytes, and monocytes using the side scattered light intensity and the fluorescence intensity in the first measurement data. Although the description is omitted here, the blood analyzer 1 can prepare a measurement sample for separately detecting neutrophils and basophils by mixing the blood specimen with predetermined reagents, and can separately detect neutrophils and basophils using measurement data obtained by measuring this measurement sample with the optical detector D. The blood analyzer 1 classifies the normal leukocytes contained in the blood specimen into five subclasses (eosinophils, neutrophils, basophils, lymphocytes, and monocytes) using the thus obtained detection result for neutrophils and basophils and the detection results for four subclasses obtained by the above-described analysis of the first measurement data. In the processing of step S152, the CPU 51a classifies mature leukocytes into subclasses using the forward scattered light, the side scattered light intensity and the fluorescence intensity in the first measurement data, and counts the number of hemocytes belonging to each of the subclasses.

In this embodiment, the range of side scattered light intensity and fluorescence intensity indicated by the dashed line in FIG. 8 is defined as a detection area A1 for an abnormal mononuclear leukocyte group. As shown in FIG. 8, the detection area A1 is set in a portion with a fluorescence intensity higher than that in the area where lymphocytes appear. As a result of experiments using clinical specimens and detailed investigation of the results of the experiments, the present inventors have found that atypical lymphocytes, abnormal lymphocytes, lymphoblasts and myeloblasts all appear in the detection area A1. Therefore, use of the detection area A1 enables highly accurate detection of the presence or absence of abnormal mononuclear leukocytes. However, it has been found that whether the detected abnormal mononuclear leukocytes are abnormal lymphocytes, blasts, or atypical lymphocytes cannot be determined with the detection area A1. In step S153, any cell group that appears within the above-described detection area A1 is detected as an abnormal mononuclear leukocyte group, and the number of hemocytes CN1 is counted.

Next, the CPU 51a determines whether CN1 is greater than a predetermined threshold T1 (step S154). The threshold T1 is a reference value for determining whether any abnormal mononuclear leukocyte is present in a blood specimen. If CN1 is greater than the threshold T1, it is determined that abnormal mononuclear leukocytes are present in the blood specimen. If CN1 is less than or equal to the threshold T1, it is determined that no abnormal mononuclear leukocytes are present in the blood specimen.

If CN1≤T1 in step S154 (NO in step S154), the CPU 51a sets a re-examination flag provided in the RAM 51c to "0" (step S155). Here, the re-examination flag is information indicating the necessity of the re-examination (the second specimen measurement conducted by the blood analyzer 1). The re-examination flag indicates that the re-examination is necessary if it is set to "1", and indicates that the re-examination is not necessary if it is set to "0". Then, the processing executed by the CPU 51a moves to step S157.

On the other hand, if CN1>T1 in step S154 (YES in step S154), the CPU 51a determines that the re-examination is necessary, and sets the re-examination flag provided in the RAM 51c to "1" (step S156). Then, the processing executed by the CPU 51a moves to step S157.

The CPU 51a stores the thus obtained analysis result (including the re-examination flag) in the hard disk 51d (step S157). Next, the CPU 51a causes the display device 52 to display an analysis result screen showing the analysis result stored in the hard disk 51d (step S158), and ends the first data processing.

The specimen analysis operation will now be described with reference to FIG. 5. After completion of the initial examination as described above, the CPU 51a of the blood analyzer 1 checks the result regarding whether the re-examination is necessary (step S3). If the re-examination of the specimen is not necessary, or in other words, if the re-examination flag is set to "0" (NO in step S3), the specimen analysis operation ends. On the other hand, if the re-examination of the specimen is necessary, or in other words, if the re-examination flag is set to "1" (YES in step S3), the blood analyzer 1 performs the re-examination of the specimen. The re-examination is an operation for determining whether a blood specimen that has undergone the initial examination contains abnormal lymphocytes, whether the blood specimen contains blasts, and whether the blood specimen contains atypical lymphocytes. This re-examination includes a first measurement process (step S4) that is the same as step S1, a second measurement process (step S5) in which a second measurement sample is measured by the measurement unit 2, and second data processing (step S6) in which the measurement data obtained in each of the first measurement process and the second measurement process is subjected to analysis processing performed by the information processing unit 5. Note that the first measurement process in the re-examination is the same as the first measurement process in the initial examination, and therefore the description thereof is omitted.

Second Measurement Process

Next, the second measurement process will now be described. The second measurement process is performed in such a manner that it partially overlaps in time with the first measurement process. In the second measurement process, the blood analyzer 1 mixes the whole blood specimen (17.0 μL), the third reagent (1000 μL), and the fourth reagent (20 μL) to prepare a second measurement sample, and measures the second measurement sample by flow cytometry using the optical detector D.

In this embodiment, the following reagents are used as the third reagent.

Third Reagent

| MOPS | 2.09 g/L |
|---|---|
| polyoxyethylene (20) oleyl ether | 1.25 g/L |
| sodium N-lauroylsarcosinate | 0.268 g/L |
| EDTA-2K | 0.5 g/L |

The above-listed ingredients were mixed, and NaOH was further added to adjust the pH to 7.3. The osmotic pressure of the third reagent was 37 mOsm/Kg, and the electric conductivity thereof was 0.745 mS/cm.

Fourth Reagent

| NK-321 | 50 mg/L |
|---|---|

NK-321 (50 mg/L) dissolved in ethylene glycol was used as the fourth reagent.

Figure 9:
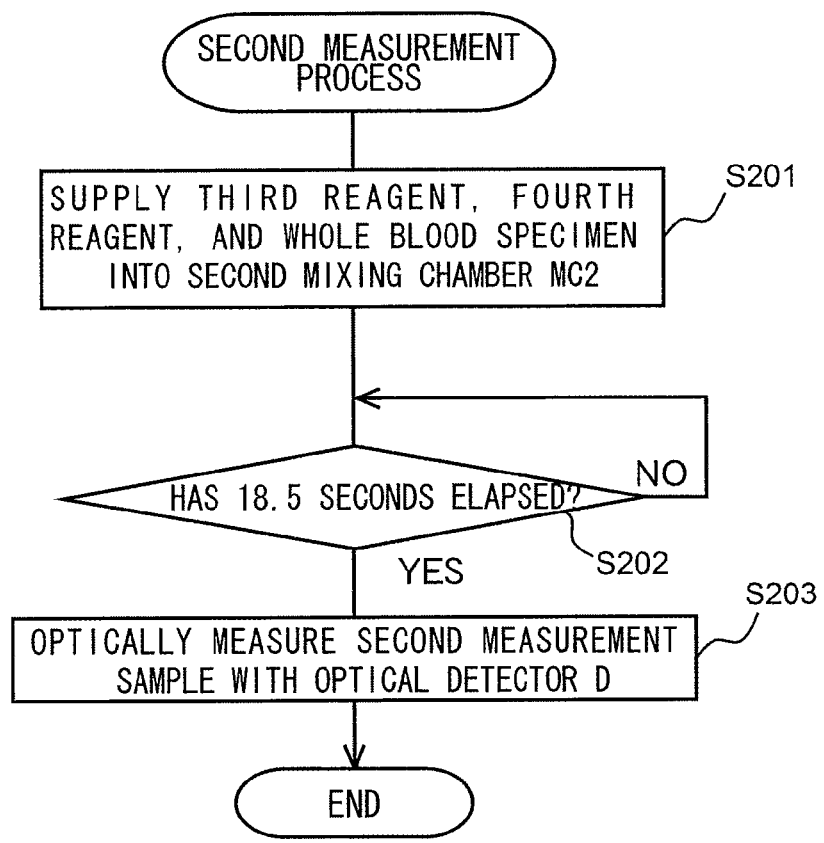
FIG. 9 is a flowchart illustrating the procedure of operation in a second measurement process performed by the blood analyzer according to the embodiment.

FIG. 9 is a flowchart illustrating the procedure of operation performed by the blood analyzer 1 in the second measurement process. First, the CPU 51a controls the measurement unit 2 to supply, to the first mixing chamber MC1, the third reagent (1000 μL) from the reagent container 222a, the fourth reagent (20 μL) from the reagent container 222b, and the whole blood specimen (17 μL) from the suction tube 211 (step S201). In step S201, the specimen supplied to the first mixing chamber MC1 is a portion of the whole blood specimen sucked by the suction tube 211 in step S101 described above. In other words, in step S101, the specimen to be supplied to the first mixing chamber MC1 and the specimen to be supplied to the second mixing chamber MC2 are sucked at a time from the specimen container T.

Next, the CPU 51a waits 18.5 seconds and determines whether 18.5 seconds have elapsed since the supply of the third reagent, the fourth reagent and the whole blood specimen to the first mixing chamber MC1 (step S202). Here, the first mixing chamber MC1 has been heated to 34.0° C. by the heater. Thus, the mixed solution of the third reagent, the fourth reagent and the blood specimen is heated at 34.0° C. for 18.5 seconds to prepare a second measurement sample.

Then, optical measurement is conducted on the second measurement sample with the optical detector D (step S203). Specifically, in the processing of step S203, the second measurement sample and the sheath fluid are simultaneously supplied to the flow cell 231 of the optical detector D. At that time, forward scattered light is received by the photodiode 243, and side scattered light is received by the photodiode 246, and fluorescence light is received by the avalanche photodiode 248. Output signals (analog signals) output from these various light-receiving elements of the optical detector D are converted into digital signals as in the first measurement process described above, and then converted into second measurement data that is digital data through predetermined signal processing. The second measurement data is transmitted to the information processing unit 5. In this signal processing, a forward scattered light signal (forward scattered light intensity), a side scattered light signal (side scattered light intensity), and a fluorescence signal (fluorescence intensity) are obtained as feature parameters contained in the second measurement data. This completes the second measurement process. As will be described later, the CPU 51a of the information processing unit 5 performs analysis processing on the second measurement data, thereby detecting abnormal lymphocytes, blasts, or atypical lymphocytes and generating analysis result data containing the detection result, and stores the analysis result data in the hard disk 51d.

Second Data Processing

Figure 10:
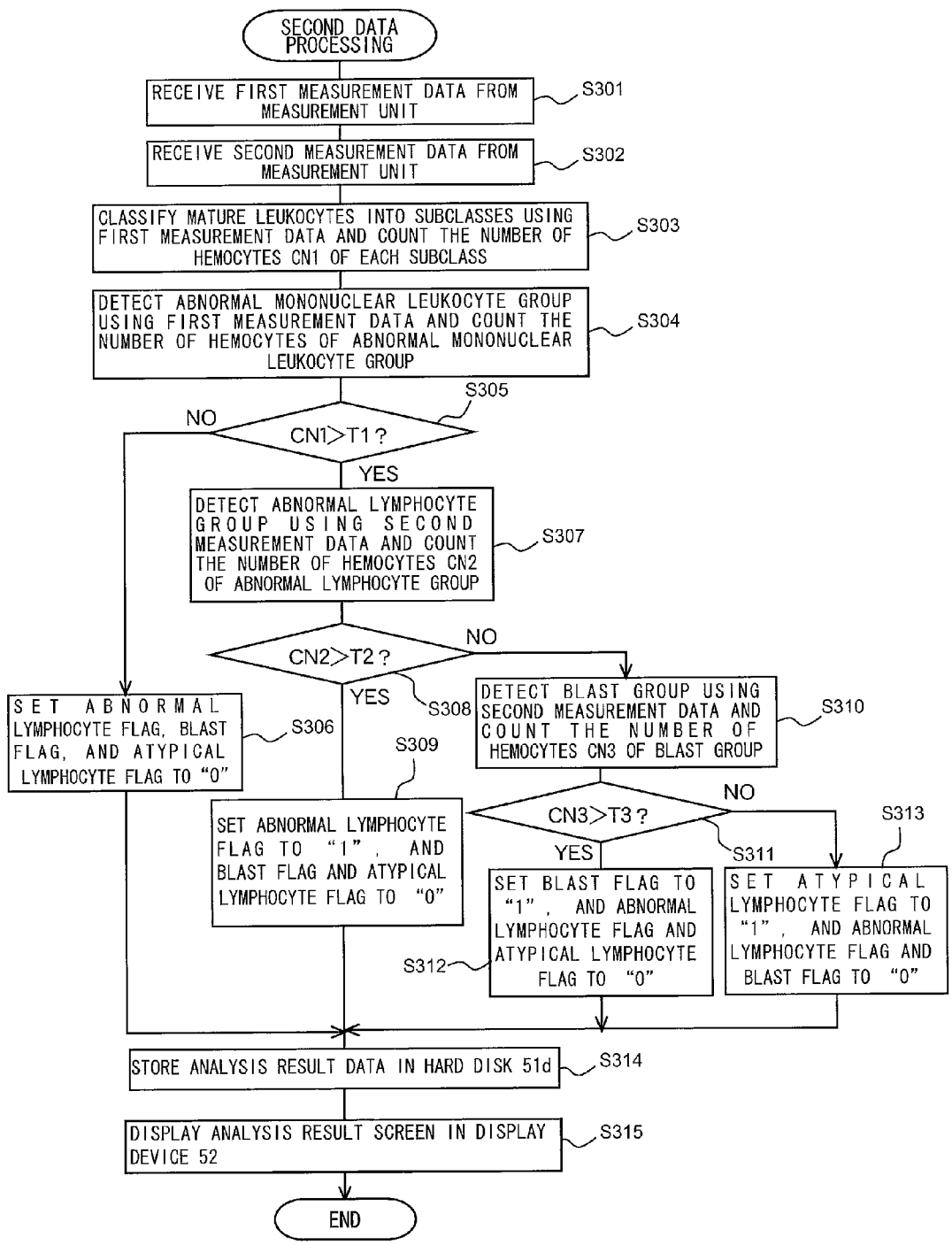
FIG. 10 is a flowchart illustrating the procedure of data processing performed by the blood analyzer according to the embodiment.

Next, the second data processing will now be described. FIG. 10 is a flowchart showing the procedure of the second data processing performed by the blood analyzer according to this embodiment. The information processing unit 5 of the blood analyzer 1 receives, from the measurement unit 2, the first measurement data (step S301) and also receives the second measurement data (step S302). The computer program 54a, which is executed by the CPU 51a, is an event-driven program, and the processing of step S303 is invoked upon occurrence of an event of receiving the first measurement data and the second measurement data.

The CPU 51a classifies the normal leukocyte into a plurality of subclasses using the first measurement data, and counts the number of hemocytes belonging to each of the subclasses (step S303). Further, the CPU 51a detects a cell group of abnormal mononuclear leukocytes (hereinafter, referred to as an "abnormal mononuclear leukocyte group") using the first measurement data, and counts the number of hemocytes CN1 contained in the detected abnormal mononuclear leukocyte group (step S304). The processing of step S303 is the same as that of step S152 described above and the processing of step S304 is the same as that of step S153 described above, and therefore the description thereof is omitted.

Next, the CPU 51a determines whether CN1 is greater than a predetermined threshold T1 (step S305). The threshold T1 is a reference value that is the same as the above-described threshold T1 in step S154. If CN1 is greater than the threshold T1, it is determined that abnormal mononuclear leukocytes are present in the blood specimen. If CN1 is less than or equal to the threshold T1, it is determined that no abnormal mononuclear leukocytes are present in the blood specimen.

If CN1≤T1 in step S305 (NO in step S305), the CPU 51a sets an abnormal lymphocyte flag, an atypical lymphocyte flag, and a blast flag that are provided in the RAM 51c to "0" (step S306). Here, the abnormal lymphocyte flag is a flag indicating the presence or absence of abnormal lymphocytes in a blood specimen. The abnormal lymphocyte flag indicates the presence of abnormal lymphocytes if it is set to "1", and indicates the absence of abnormal lymphocytes if it is set to "0". The atypical lymphocyte flag is a flag indicating the presence or absence of atypical lymphocytes in the blood specimen. The atypical lymphocyte flag indicates the presence of atypical lymphocytes if it is set to "1", and indicates the absence of atypical lymphocytes if it is set to "0". Likewise, the blast flag is a flag indicating the presence or absence of blasts in the blood specimen. The blast flag indicates the presence of blasts if it is set to "1", and indicates the absence of blasts if it is set to "0". Then, the processing executed by the CPU 51a moves to step S314.

On the other hand, if CN1>T1 in step S305 (YES in step S305), the CPU 51a detects a cell group of abnormal lymphocytes (hereinafter, referred to as an "abnormal lymphocyte group") using the second measurement data, and counts the number of hemocytes CN2 contained in the detected abnormal lymphocyte group (step S307).

Figure 11:
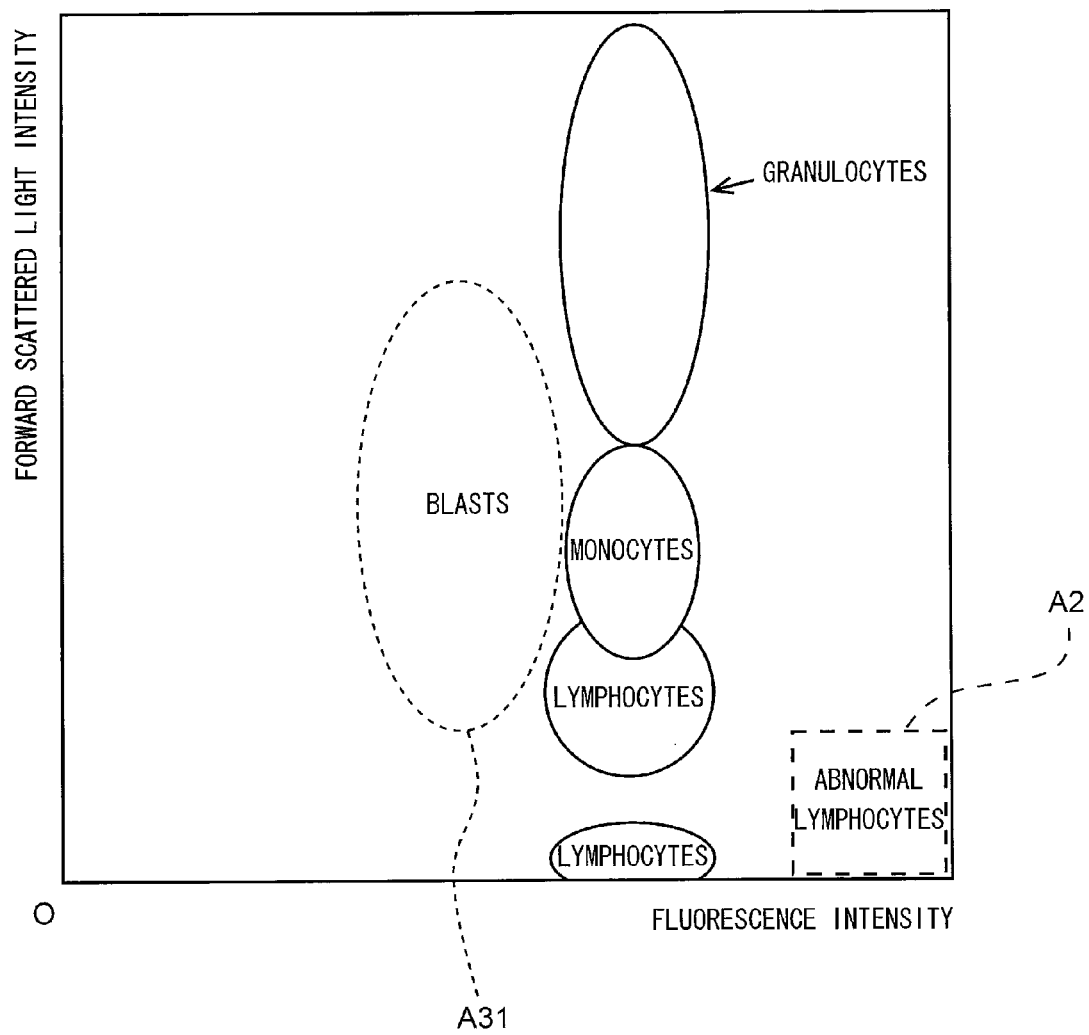
FIG. 11 is a scattergram of forward scattered light intensity and fluorescence intensity in second measurement data.
Figure 12:
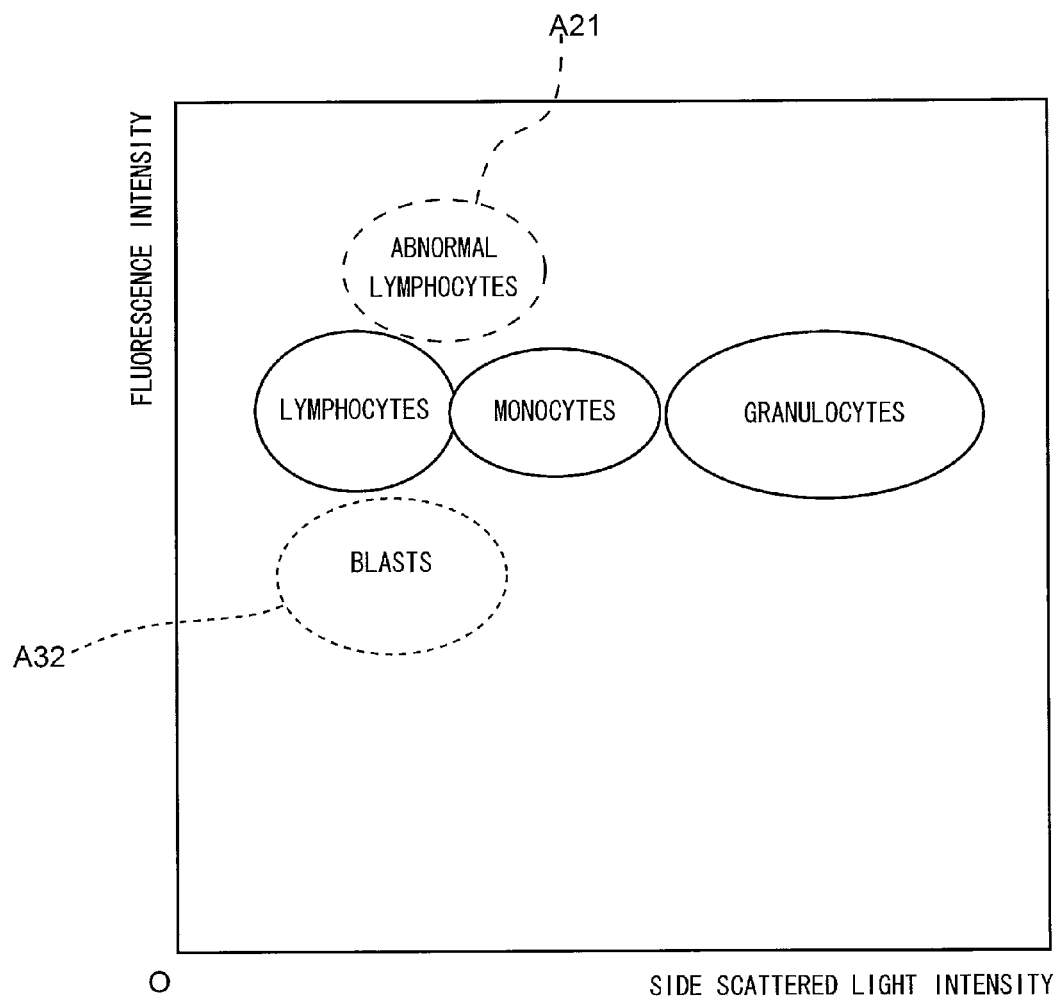
FIG. 12 is a scattergram of side scattered light intensity and fluorescence intensity in the second measurement data.

The processing of step S307 will now be described in detail. FIG. 11 is a scattergram of forward scattered light intensity and fluorescence intensity in the second measurement data, and FIG. 12 is a scattergram of side scattered light intensity and fluorescence intensity in the second measurement data. A cluster of blasts, a cluster of granulocytes (a hemocyte group consisting of neutrophils, eosinophils, and basophils), a cluster of lymphocytes, and a cluster of monocytes appear in the scattergram of forward scattered light intensity and fluorescence intensity in the second measurement data shown in FIG. 11. A cluster of blasts, a cluster of granulocytes, a cluster of lymphocytes, and a cluster of monocytes appear also in the scattergram of side scattered light intensity and fluorescence intensity in the second measurement data shown in FIG. 12.

In this embodiment, the range of forward scattered light intensity and fluorescence intensity indicated by the dashed line in FIG. 11 is defined as a detection area A2 for an abnormal lymphocyte group. As shown in FIG. 11, the detection area A2 is set in a portion with a fluorescence intensity higher than that in the area where lymphocytes and monocytes appear. As a result of experiments using clinical specimens and detailed investigation of the results of the experiments, the present inventors have found that abnormal lymphocytes appear in the detection area A2 and an area A21 as shown in FIG. 12, and that blasts appear in an area A31 as shown in FIG. 11 and an area A32 as shown in FIG. 12. As a result of detailed evaluation of the experiment results, the present inventors have also found that in the scattergram of forward scattered light intensity and fluorescence intensity and the scattergram of side scattered light intensity and fluorescence intensity in the second measurement data, atypical lymphocytes do not appear in any of the above-mentioned areas A2, A21, A31, and A32, but appear in the areas where normal leukocytes appear. Therefore, use of the area A2 shown in FIG. 11 or the area A21 shown in FIG. 12 allows abnormal lymphocytes to be detected distinguishably from atypical lymphocytes and blasts. In step S307, any cell group that appears within the above-described detection area A2 is detected as an abnormal lymphocyte group, and the number of hemocytes CN2 is counted.

Next, the CPU 51a determines whether CN2 is greater than a predetermined threshold T2 (step S308). The threshold T2 is a reference value for determining whether any abnormal lymphocyte is present in a blood specimen. In step S308, if CN2 is greater than the threshold T2, it is determined that abnormal lymphocytes are present in the blood specimen. If CN2 is less than or equal to the threshold T2, it is determined that no abnormal lymphocytes are present in the blood specimen.

If CN2>T2 in step S308 (YES in step S308), the CPU 51a sets the abnormal lymphocyte flag provided in the RAM 51c to "1", and sets each of the atypical lymphocyte flag and the blast flag to "0" (step S309). Then, the processing executed by the CPU 51a moves to step S314.

On the other hand, if CN2≤T2 in step S308 (NO in step S308), the CPU 51a detects a cell group of blasts (hereinafter, referred to as a "blast group") using the second measurement data, and counts the number of hemocytes CN3 contained in the detected blast group (step S310).

Figure 13:
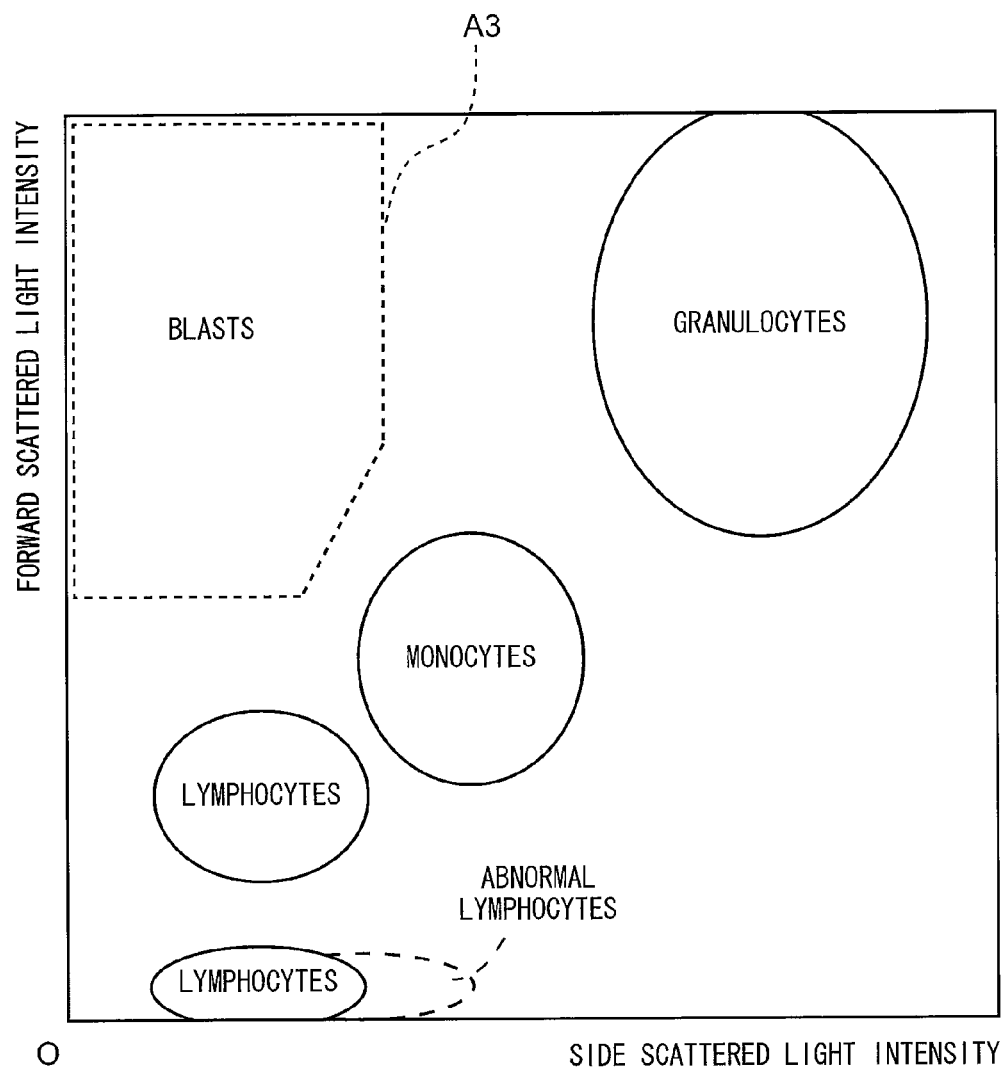
FIG. 13 is a scattergram of forward scattered light intensity and side scattered light intensity in the second measurement data.

The processing of step S310 will now be described in detail. FIG. 13 is a scattergram of forward scattered light intensity and side scattered light intensity in the second measurement data. A cluster of granulocytes, a cluster of lymphocytes, and a cluster of monocytes appear in the scattergram of forward scattered light intensity and side scattered light intensity in the second measurement data shown in FIG. 13. In this embodiment, the range of forward scattered light intensity and side scattered light intensity indicated by the dashed line in FIG. 13 is defined as a detection area A3 for the blast group. As shown in FIG. 13, the detection area A3 is set in a portion with a forward scattered light intensity higher than that in the area where lymphocytes appear. As a result of experiments using clinical specimens and detailed investigation of the results of the experiments, the present inventors have found that blasts appear in the detection area A3, and that abnormal lymphocytes and atypical lymphocytes do not appear in the detection area A3. Therefore, use of the detection area A3 allows blasts to be detected distinguishably from abnormal lymphocytes and atypical lymphocytes. In step S310, any cell group that appears within the above-described detection area A3 is detected as a blast group, and the number of hemocytes CN3 is counted. As described above, the present inventors have also found that blasts appear in the area A31 shown in FIG. 11 and the area A32 shown in FIG. 12, and abnormal lymphocytes and atypical lymphocytes do not appear in these areas. Therefore, the area A31 or the area A32 may be used to detect blasts distinguishably from abnormal lymphocytes and atypical lymphocytes.

Next, the CPU 51a determines whether CN3 is greater than a predetermined threshold T3 (step S311). The threshold T3 is a reference value for determining whether any blast is present in a blood specimen. In step S311, if CN3 is greater than the threshold T3, it is determined that blasts are present in the blood specimen. If CN3 is less than or equal to the threshold T3, it is determined that no blasts are present in the blood specimen. When the processing of step S311 is performed, it is already determined in step S305 that abnormal mononuclear leukocytes are present in the blood specimen and it is already determined in step S308 that no abnormal lymphocytes are present in the blood specimen. Accordingly, if CN3 is less than or equal to the threshold T3 in step S311, it is determined that atypical lymphocytes are present in the blood specimen.

In other words, if it is determined in step S308 or step S311 that CN2>T2 or CN3>T3 after it is determined in step S305 that abnormal mononuclear leukocytes are present in the blood specimen, this means that it is determined that the abnormal mononuclear leukocytes present in the blood specimen are neoplastic abnormal mononuclear leukocytes (abnormal mononuclear leukocytes derived from a hematopoietic system disease). On the other hand, if it is determined in step S308 and step S311 that CN2≤T2 and CN3≤T3 after it is determined in step S305 that abnormal mononuclear leukocytes are present in the blood specimen, this means that it is determined that the abnormal mononuclear leukocytes present in the blood specimen are reactive abnormal mononuclear leukocytes.

If CN3>T3 in step S311 (YES in step S311), the CPU 51a sets the blast flag provided in the RAM 51c to "1", and sets each of the abnormal lymphocyte flag and the atypical lymphocyte flag to "0" (step S312). Then, the processing executed by the CPU 51a moves to step S314.

On the other hand, if CN3≤T3 in step S311 (NO in step S311), the CPU 51a sets the atypical lymphocyte flag provided in the RAM 51c to "1", and sets each of the abnormal lymphocyte flag and the blast flag to "0" (step S313). Then, the processing executed by the CPU 51a moves to step S314.

The CPU 51a stores the thus obtained analysis result (including the abnormal lymphocyte flag, the atypical lymphocyte flag, and the blast flag) in the hard disk 51d (step S314). Next, the CPU 51a causes the display device 52 to display an analysis result screen showing the analysis result stored in the hard disk 51d (step S315), and ends the second data processing.

When the above-described re-examination ends, the specimen analysis operation ends.

Next, examples of scattergrams obtained when measuring a specific blood specimen by the above-described re-examination are shown, and the analysis of the measurement data performed by the blood analyzer 1 according to this embodiment will now be described. FIGS. 14A to 14D show examples of scattergrams obtained by the blood analyzer 1. FIG. 14A shows examples of scattergrams obtained when measuring a blood specimen A collected from a patient with acute myelocytic leukemia. FIG. 14B shows examples of scattergrams obtained when measuring a blood specimen B collected from a patient with chronic lymphocytic leukemia. FIG. 14C shows examples of scattergrams obtained when measuring a blood specimen C containing atypical lymphocytes. FIG. 14D shows examples of scattergrams obtained when measuring a normal blood specimen D.

Myeloblasts appear in the peripheral blood of a patient with acute myelocytic leukemia. As shown in FIG. 14A, particles corresponding to the detected hemocytes are present in the detection area A1 for the abnormal mononuclear leukocyte group in a scattergram SG11 of side scattered light intensity and fluorescence intensity (scattergram for leukocyte classification) in the first measurement data of the blood specimen A. That is, as can be seen from the scattergram SG11, the abnormal mononuclear leukocyte group is detected in the blood specimen A. Particles corresponding to the detected hemocytes are substantially absent (they are present in a very small amount, but the number of hemocytes does not exceed the threshold T2) in the detection area A2 for abnormal lymphocytes in a scattergram SG12 of forward scattered light intensity and fluorescence intensity (scattergram for abnormal lymphocyte detection) in the second measurement data of the blood specimen A. FIG. 14A also shows a scattergram SG13 of side scattered light intensity and fluorescence intensity in the second measurement data of the blood specimen A for reference. It can be seen that in the scattergram SG13 as well, hemocytes are substantially absent in the area A21 where abnormal lymphocytes appear. Furthermore, particles corresponding to the detected hemocytes are present in the detection area A3 for blasts in a scattergram SG14 of forward scattered light intensity and side scattered light intensity (scattergram for blast detection) in the second measurement data of the blood specimen A. That is, as can be seen from the scattergram SG14, the blast group is detected in the blood specimen A. Thus, CN1>T1, CN2≤T2, and CN3>T3 when the blood analyzer 1 according to this embodiment analyses the blood specimen A, and therefore it is determined that blasts are present.

Abnormal lymphocytes, which are mature lymphocytic leukemia cells, appear in the peripheral blood of a patient with chronic lymphocytic leukemia. As shown in FIG. 14B, particles corresponding to the detected hemocytes are present in the detection area A1 for the abnormal mononuclear leukocyte group in a scattergram SG21 for leukocyte classification of the blood specimen B. That is, as can be seen from the scattergram SG21, the abnormal mononuclear leukocyte group is detected in the blood specimen B. Particles corresponding to the detected hemocytes are present in the detection area A2 for abnormal lymphocytes in a scattergram SG22 for abnormal lymphocyte detection in the second measurement data of the blood specimen B. FIG. 14B also shows a scattergram SG23 of side scattered light intensity and fluorescence intensity in the second measurement data of the blood specimen B for reference. It can be seen that in the scattergram SG23 as well, hemocytes are present in the area A21 where abnormal lymphocytes appear. Furthermore, particles corresponding to the detected hemocytes are substantially absent in the detection area A3 for blasts in a scattergram SG24 for blast detection in the second measurement data of the blood specimen B. That is, as can be seen from the scattergram SG22, the abnormal lymphocyte group is detected in the blood specimen B. Thus, CN1>T1 and CN2>T2 when the blood analyzer 1 according to this embodiment analyses the blood specimen B, and therefore it is determined that abnormal lymphocytes are present.

As shown in FIG. 14C, particles corresponding to the detected hemocytes are present in the detection area A1 for the abnormal mononuclear leukocyte group in a scattergram SG31 for leukocyte classification of the blood specimen C containing atypical lymphocytes. That is, as can be seen from the scattergram SG31, the abnormal mononuclear leukocyte group is detected in the blood specimen C. Particles corresponding to the detected hemocytes are substantially absent in the detection area A2 for abnormal lymphocytes in a scattergram SG32 for abnormal lymphocyte detection in the second measurement data of the blood specimen C. FIG. 14C also shows a scattergram SG33 of side scattered light intensity and fluorescence intensity in the second measurement data of the blood specimen C for reference. It can be seen that in the scattergram SG33 as well, hemocytes are substantially absent in the area A21 where abnormal lymphocytes appear. Furthermore, particles corresponding to the detected hemocytes are substantially absent in the detection area A3 for blasts in a scattergram SG34 for blast detection in the second measurement data of the blood specimen C. That is, as can be seen from the scattergrams SG32 and SG34, neither the abnormal lymphocyte group nor the blast group is detected in the blood specimen C. Thus, CN1>T1, CN2≤T2, and CN3≤T3 when the blood analyzer 1 according to this embodiment analyses the blood specimen C, and therefore it is determined that atypical lymphocytes are present.

Abnormal mononuclear leukocytes do not appear in normal peripheral blood. As shown in FIG. 14D, particles corresponding to the detected hemocytes are substantially absent in the detection area A1 for the abnormal mononuclear leukocyte group in a scattergram SG41 for leukocyte classification of the blood specimen D. That is, as can be seen from the scattergram SG41, the abnormal mononuclear leukocyte group is not detected in the blood specimen D. Particles corresponding to the detected hemocytes are substantially absent in the detection area A2 for abnormal lymphocytes in a scattergram SG42 for abnormal lymphocyte detection in the second measurement data of the blood specimen D. FIG. 14D also shows a scattergram SG43 of side scattered light intensity and fluorescence intensity in the second measurement data of the blood specimen D for reference. It can be seen that in the scattergram SG43 as well, hemocytes are substantially absent in the area A21 where abnormal lymphocytes appear. Furthermore, particles corresponding to the detected hemocytes are substantially absent in the detection area A3 for blasts in a scattergram SG44 for blast detection in the second measurement data of the blood specimen D. That is, as can be seen from the scattergrams SG42 and SG44, neither the abnormal lymphocyte group nor the blast group is detected in the blood specimen D. Thus, CN1≤T1 when the blood analyzer 1 according to this embodiment analyses the blood specimen D, and therefore it is determined that no abnormal mononuclear leukocytes are present.

Figure 15:
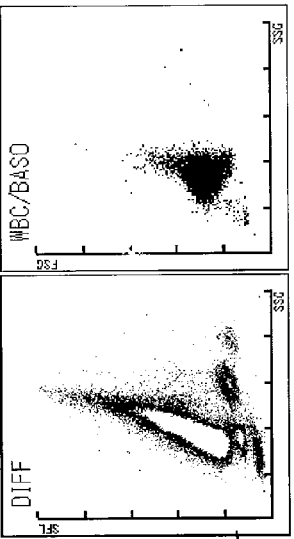
FIG. 15 is a diagram showing an example of an analysis result screen of the blood analyzer according to the embodiment.

FIG. 15 is a diagram showing an example of an analysis result screen of the blood analyzer 1. FIG. 15 shows an analysis result screen for the blood specimen B. As shown in FIG. 15, the measured numeric data of the measurement items (WBC, RBC, PLT, etc.) are displayed on an analysis result screen R1. The blood specimen B contains abnormal lymphocytes. In the analysis result data relating to the blood specimen B, the abnormal lymphocyte flag is set to "1", and the blast flag and the atypical lymphocyte flag are each set to "0". Accordingly, as shown in FIG. 15, the indication "Abn Lympho?", which is information indicating the possibility that abnormal lymphocytes are present, is added to the Flag field FLG on the analysis result screen R1 for the blood specimen B. Although not shown here, when the blast flag is set to "1" and each of the abnormal lymphocyte flag and the atypical lymphocyte flag is set to "0", "Blasts?" is indicated in the flag indication field FLG. When the atypical lymphocyte flag is set to "1" and the abnormal lymphocyte flag and the blast flag are each set to "0", "Atypical Lympho?" is indicated in the flag indication field FLG. Furthermore, when the abnormal lymphocyte flag, the blast flag, and the atypical lymphocyte flag are all set to "0", none of "Abn Lympho?", "Blasts?", and "Atypical Lympho?" above will be indicated on the analysis result screen. This enables the operator to understand whether any abnormal lymphocyte is detected in the blood specimen, whether any blast is detected in the blood specimen, and whether any atypical lymphocyte is detected in the blood specimen by just looking at the analysis result screen. In addition, the scattergram SG21 of side scattered light intensity and fluorescence intensity of the first measurement data is indicated on the analysis result screen R1. Furthermore, the scattergram SG23 of side scattered light intensity and fluorescence intensity of the second measurement data is indicated on the analysis result screen R1. By referring to these scattergrams, the operator can understand the basis of the detection results obtained by the blood analyzer 1 for abnormal lymphocytes, blasts, atypical lymphocytes. The operator can also determine the validity of the detection results for abnormal lymphocytes, blasts, and atypical lymphocyte obtained by the blood analyzer 1.

With the configuration described above, the blood analyzer 1 can detect abnormal mononuclear leukocytes by measuring, with the optical detector D, the first measurement sample prepared by mixing the blood specimen, the first reagent containing a hemolyzing agent, and the second reagent containing a fluorescent dye for staining nucleic acid. Furthermore, when abnormal mononuclear leukocytes are detected, the blood analyzer 1 can determine whether the abnormal mononuclear leukocytes are abnormal lymphocytes, blasts, or atypical lymphocytes by measuring, with the optical detector D, the second measurement sample prepared by mixing the blood specimen, the third reagent containing a hemolyzing agent, and the fourth reagent containing a fluorescent dye for staining nucleic acid.

Other Embodiments

Note that the reaction temperature and the reaction time during mixing of the blood specimen, the first reagent, and the second reagent, as well as during mixing of the blood specimen, the third reagent, and the fourth reagent in the sample preparation portion 22 may be suitably set according to the state of damage and staining of the hemocytes contained in the blood specimen, without any particular limitation. Specifically, the reaction time and the reaction temperature may be adjusted such that the reaction time is short when the reaction temperature is high and the reaction time is long when the reaction temperature is low. More specifically, it is preferable that the blood specimen and the reagents are mixed at a temperature of 20° C. to 45° C. for 3 to 40 seconds.

Although the above-described embodiment has addressed a configuration in which the third reagent containing a hemolyzing agent and the fourth reagent containing a fluorescent dye that can stain nucleic acid are used to perform the second measurement process, the present invention is not limited thereto. It is possible to adopt a configuration in which the second measurement sample is prepared by mixing the blood specimen with a single reagent containing a hemolyzing agent and a nucleic acid staining dye, and abnormal lymphocytes, blasts, and atypical lymphocytes are detected using the second measurement sample. In this case, the concentrations of the surfactant, the solubilizing agent, and the fluorescent dye are adjusted to the above-described concentrations when the reagents have been mixed.

Although the above-described embodiment has addressed a configuration in which the abnormal mononuclear cell is detected based on the side scattered light intensity and the fluorescent intensity in the first measurement data, the abnormal mononuclear cell can be detected based on a forward scattered light intensity and the fluorescent intensity.

Although the above-described embodiment has addressed a configuration in which the presence or absence of abnormal mononuclear leukocytes in the blood specimen is determined based on whether the number of hemocytes CN1 appeared within the detection area A1 is greater than the threshold T1 for abnormal mononuclear leukocytes with respect to side scattered light intensity and fluorescence intensity in the first measurement data, the present invention is not limited thereto. It is possible to adopt a configuration in which the ratio of the number of hemocytes appeared within the detection area A1 for abnormal mononuclear leukocytes to the total number of leukocytes is obtained with respect to side scattered light intensity and fluorescence intensity in the first measurement data, and whether abnormal mononuclear leukocytes are present is determined by determining whether the obtained ratio is greater than a predetermined reference value. For detection of abnormal lymphocytes as well, it is also possible to adopt a configuration in which the ratio of the number of hemocytes appeared within the detection area A2 for abnormal lymphocytes to the total number of leukocytes is obtained with respect to forward scattered light intensity and fluorescence intensity in the second measurement data, and whether abnormal lymphocytes are present is determined by determining whether the obtained ratio is greater than a predetermined reference value. Likewise, for detection of blasts as well, it is also possible to adopt a configuration in which the ratio of the number of hemocytes appeared within the detection area A3 for blasts to the total number of leukocytes is obtained with respect to forward scattered light intensity and side scattered light intensity in the second measurement data, and whether any blast is present is determined by determining whether the obtained ratio is greater than a predetermined reference value.

Although the above-described embodiment has addressed a configuration in which the second measurement sample is optically measured with a flow cytometer to obtain an optical signal including fluorescence intensity, forward scattered light intensity, and side scattered light intensity, and optical signal is used to determine whether any abnormal lymphocyte is present in a blood specimen, whether any blast is present in a blood specimen, and whether any atypical lymphocyte is present in a blood specimen, the present invention is not limited thereto. It is also possible to adopt a configuration in which scattered light information other than forward scattered light intensity and side scattered light intensity, such as wide angle forward scattered light intensity, is obtained along with fluorescence intensity, and the scattered light information and the fluorescence intensity are used to determine whether abnormal lymphocytes are present in a blood specimen, whether any blast is present in a blood specimen, and whether any atypical lymphocyte is present in a blood specimen. Likewise, for the optical measurement of the first measurement sample as well, it is also possible to adopt a configuration in which scattered light information relating to scattered light (e.g., wide angle forward scattered light intensity) other than forward scattered light intensity and side scattered light intensity is obtained along with fluorescence intensity, and the scattered light information and the fluorescence intensity are used for classification of leukocytes and detection of abnormal mononuclear leukocytes.

Although the above-described embodiment has addressed a configuration in which the control of the measurement unit 2 and the processing of the measurement data are performed by the CPU 51a executing the above-described computer program 54a, the present invention is not limited thereto. It is also possible to adopt a configuration in which the control of the measurement unit 2 and the processing of measurement data are performed by dedicated hardware, such as FPGA or ASIC, that can perform the same processing as that performed by the computer program 54a.

Although the above-described embodiment has addressed a configuration in which a single computer 5a executes all the processing of the computer program 54a, the present invention is not limited thereto. It is also possible to adopt a distributed system in which the same processing as that of the above-described computer program 54a is executed by a plurality of devices (computers) in a distributed manner.

Although the above-described embodiment has addressed a configuration in which whether any blast is present in a blood specimen is determined after determining that no abnormal lymphocytes are present as a result of determining whether any abnormal lymphocyte is present in the blood specimen, the present invention is not limited thereto. It is also possible to first determine whether any blast is present in a blood specimen and then determine whether any abnormal lymphocyte is present in the blood specimen after having being determined that no blasts are present. This also enables the operator to determine whether the abnormal mononuclear leukocyte is an abnormal lymphocyte, a blast, or an atypical lymphocyte.

Although the above-described embodiment has addressed a configuration in which the first measurement sample is measured in the initial examination, whether any abnormal mononuclear leukocyte is present in a blood specimen is determined, and, if it is determined that abnormal mononuclear leukocytes are present, the second measurement sample is measured in the re-examination, thereby determining whether any abnormal lymphocyte is present in the blood specimen, whether any blast is present in the blood specimen, and whether any atypical lymphocyte is present in the blood specimen, the present invention is not limited thereto. It is possible to adopt a configuration in which the first measurement process and the second measurement process are performed in the first specimen measurement (initial examination), whether any abnormal mononuclear leukocyte is present in the blood specimen is determined based on the first measurement data obtained in the first measurement process, and, if it is determined that abnormal mononuclear leukocytes are present, whether any abnormal lymphocyte is present in the blood specimen, whether any blast is present in the blood specimen, and whether any atypical lymphocyte is present in the blood specimen are determined based on the second measurement data obtained in the second measurement process (i.e., a configuration in which an operation corresponding to the re-examination of the above-described embodiment is performed in the initial examination). Although the above-described embodiment has addressed a configuration in which the first measurement process is performed also in the re-examination, and whether any abnormal mononuclear leukocyte is present in the blood specimen is determined, the present invention is not limited thereto. It is possible to adopt a configuration in which only the second measurement process is performed in the re-examination, and the second measurement data thus obtained is used to determine whether any abnormal lymphocyte is present in the blood specimen, whether any blast is present in the blood specimen, and whether any atypical lymphocyte is present in the blood specimen.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A blood analyzer comprising:
a dispensing portion configured to dispense a first blood specimen and a second blood specimen from a blood specimen;
a sample preparation portion configured to prepare a first measurement sample from the first blood specimen dispensed by the dispensing portion, a first fluorescent dye for staining nucleic acid, and a first hemolyzing agent containing a cationic surfactant, and configured to prepare a second measurement sample from the second blood specimen dispensed by the dispensing portion, a second fluorescent dye for staining nucleic acid, and a second hemolyzing agent not containing a cationic surfactant but containing another surfactant;
a light source configured to irradiate light onto each of the first measurement sample and the second measurement sample prepared by the sample preparation portion;
a light-receiving portion configured to receive a first fluorescence and a first scattered light from the first measurement sample irradiated with light by the light source and output a first fluorescence signal relating to the received first fluorescence and a first scattered light signal relating to the received first scattered light, and configured to receive a second fluorescence, a second scattered light and a third scattered light from the second measurement sample irradiated with light by the light source and output a second fluorescence signal relating to the received second fluorescence, a second scattered light signal relating to the received second scattered light and a third scattered light signal relating to the received third scattered light;
an information processing portion configured to distinguishably detect an atypical lymphocyte, an abnormal lymphocyte and a blast from the blood specimen based on the first fluorescence signal, the first scattered light signal, the second fluorescence signal, the second scattered light signal and a third scattered light signal; and
an output portion configured to output a result of the detection made by the information processing portion,
the information processing portion distinguishably detecting the abnormal lymphocyte based on the second fluorescence signal, and
the information processing portion distinguishably detecting the blast based on the second scattered light signal and the third scattered light signal.

2. The blood analyzer according to claim 1,
wherein the information processing portion detects a cell which is any one of the atypical lymphocyte, the abnormal lymphocyte, and the blast based on the first fluorescence signal and the first scattered light signal.

3. The blood analyzer according to claim 2,
wherein the information processing portion controls the dispensing portion and the sample preparation portion so as to dispense the second blood specimen from the blood specimen and prepares the second measurement sample, when the cell which is any one of the atypical lymphocyte, the abnormal lymphocyte, and the blast has been detected from the blood specimen.

4. The blood analyzer according to claim 2,
wherein the information processing portion classifies leukocytes contained in the blood specimen into a plurality of types and detects the cell which is any one of the atypical lymphocyte, the abnormal lymphocyte, and the blast, based on the first fluorescence signal and the first scattered light signal.

5. The blood analyzer according to claim 2,
wherein the information processing portion detects, as the cell which is any one of the atypical lymphocyte, the abnormal lymphocyte, and the blast, a cell indicating a predetermined range of fluorescence intensity and scattered light intensity, based on the first fluorescence signal and the first scattered light signal.

6. The blood analyzer according to claim 5,
wherein the predetermined range of fluorescence intensity is greater than fluorescence intensity which is obtained from a normal lymphocyte.

7. The blood analyzer according to claim 5,
wherein the information processing portion obtains a value reflecting a number of cells which indicate the predetermined range of fluorescence intensity and scattered light intensity, and compares the obtained value and a predetermined threshold value to detect the cell indicating the predetermined range of fluorescence intensity and scattered light intensity.

8. The blood analyzer according to claim 1,
wherein the information processing portion detects, as the abnormal lymphocyte, a cell indicating greater fluorescence intensity, based on the second fluorescence signal, than fluorescence intensity obtained from a normal lymphocyte.

9. The blood analyzer according to claim 1,
wherein the information processing portion detects, as the abnormal lymphocyte, a cell indicating a predetermined range of fluorescence intensity based on the second fluorescence signal, and obtains a value reflecting a number of cells which indicate the predetermined range of fluorescence intensity, and compares the obtained value and a predetermined threshold value to detect the cell indicating the predetermined range of fluorescence intensity.

10. The blood analyzer according to claim 2,
wherein the light-receiving portion receives a forward scattered light and a side scattered light from the second measurement sample irradiated with light by the light source, and outputs the second scattered light signal including a forward scattered light signal relating to the received forward scattered light and a side scattered light signal relating to the received side scattered light, and the information processing portion detects, as the blast, a cell indicating a predetermined range of forward scattered light intensity and side scattered light intensity, based on the forward scattered light signal and the side scattered light signal.

11. The blood analyzer according to claim 2,
wherein the information processing portion detects the atypical lymphocyte from the blood specimen, when any of the abnormal lymphocyte and the blast has not been detected from the blood specimen based on the second fluorescence signal and the second scattered light signal.

12. The blood analyzer according to claim 1,
wherein the another surfactant contained in the second hemolyzing agent is a nonionic surfactant.

13. A blood analyzer comprising:
a dispensing portion configured to dispense a first blood specimen and a second blood specimen from a blood specimen;
a sample preparation portion configured to prepare a first measurement sample from the first blood specimen dispensed by the dispensing portion, a first fluorescent dye for staining nucleic acid, and a first hemolyzing agent containing a cationic surfactant, and configured to prepare a second measurement sample from the second blood specimen dispensed by the dispensing portion, a second fluorescent dye for staining nucleic acid, and a second hemolyzing agent not containing a cationic surfactant but containing another surfactant;
a light source configured to irradiate light onto each of the first measurement sample and the second measurement sample prepared by the sample preparation portion;
a light-receiving portion configured to receive a first fluorescence and a first scattered light from the first measurement sample irradiated with light by the light source and output a first fluorescence signal relating to the received first fluorescence and a first scattered light signal relating to the received first scattered light, and configured to receive a second fluorescence and a second scattered light from the second measurement sample irradiated with light by the light source and output a second fluorescence signal relating to the received second fluorescence and a second scattered light signal relating to the received second scattered light;
an information processing portion configured to distinguishably detect an atypical lymphocyte, an abnormal lymphocyte and a blast, based on the first fluorescence signal, the first scattered light signal, the second fluorescence signal and the second scattered light signal; and
an output portion configured to output a result of the detection made by the information processing portion,
wherein the information processing portion detects, as the abnormal lymphocyte, a cell indicating greater fluorescence intensity than fluorescence intensity obtained from a normal lymphocyte, and
wherein the information processing portion detects, as the blast, a cell indicating lower fluorescence intensity than fluorescence intensity obtained from a normal lymphocyte.

14. The blood analyzer according to claim 13,
wherein the information processing portion detects an abnormal mononuclear leukocyte from the blood specimen based on the first fluorescence signal and the first scattered light signal, and distinguishably detects the atypical lymphocyte, the abnormal lymphocyte and the blast based on the second fluorescence signal and the second scattered light signal when the abnormal mononuclear leukocyte has been detected from the blood specimen.

15. The blood analyzer according to claim 14,
wherein the information processing portion classifies leukocytes contained in the blood specimen into a plurality of types and detects the abnormal mononuclear leukocyte from the blood specimen, based on the first fluorescence signal and the first scattered light signal.

16. The blood analyzer according to claim 14,
wherein the information processing portion detects, as the abnormal mononuclear leukocyte, a cell indicating a predetermined range of fluorescence intensity and scattered light intensity, based on the first fluorescence signal and the first scattered light signal.

17. The blood analyzer according to claim 14, wherein the information processing portion controls the dispensing portion and the sample preparation portion so as to dispense the second blood specimen from the blood specimen and prepares the second measurement sample, when the abnormal mononuclear leukocyte has been detected from the blood specimen.

18. The blood analyzer according to claim 14, wherein the information processing portion detects the atypical lymphocyte in the blood specimen, when the abnormal lymphocyte and the blast have not been detected in the blood specimen based on the second fluorescence signal and the second scattered light signal.

19. A blood analyzer comprising:
a dispensing portion configured to dispense a first blood specimen and a second blood specimen from a blood specimen;
a sample preparation portion configured to prepare a first measurement sample from the first blood specimen dispensed by the dispensing portion, a first fluorescent dye for staining nucleic acid, and a first hemolyzing agent containing a cationic surfactant, and configured to prepare a second measurement sample from the second blood specimen dispensed by the dispensing portion, a second fluorescent dye for staining nucleic acid, and a second hemolyzing agent not containing a cationic surfactant but containing another surfactant;
a light source configured to irradiate light onto each of the first measurement sample and the second measurement sample prepared by the sample preparation portion;
a light-receiving portion configured to receive a first fluorescence and a first scattered light from the first measurement sample irradiated with light by the light source and output a first fluorescence signal relating to the received first fluorescence and a first scattered light signal relating to the received first scattered light, and configured to receive a second fluorescence, a second scattered light and a third scattered light from the second measurement sample irradiated with light by the light source and output a second fluorescence signal relating to the received second fluorescence, a second scattered light signal relating to the received second scattered light and a third scattered light signal relating to the received third scattered light;
an information processing portion configured to
detect an abnormal mononuclear leukocyte based on the first fluorescence signal and the first scattered light signal,
distinguishably detect the abnormal lymphocyte based on the second fluorescence signal when the abnormal mononuclear leukocyte is detected, distinguishably detect the blast based on the second scattered light signal and the third scattered light signal when the abnormal mononuclear leukocyte is detected and the abnormal lymphocyte is not detected, and distinguishably detect the atypical lymphocyte when the abnormal mononuclear leukocyte is detected and any of the abnormal lymphocyte and the blast is not detected; and an output portion configured to output a result of the detection made by the information processing portion.

20. The blood analyzer according to claim 13, wherein the information processing portion distinguishably detects an abnormal mononuclear leukocyte based on the first fluorescence signal and the first scattered light signal, performs the detection of the cell as the abnormal lymphocyte when the abnormal mononuclear leukocyte is detected, performs the detection of the cell as the blast when the abnormal mononuclear leukocyte is detected and the abnormal lymphocyte is not detected, and detects the atypical lymphocyte when the abnormal mononuclear leukocyte is detected and any of the abnormal lymphocyte and the blast is not detected.

* * * * *